(12) United States Patent
Chernov et al.

(10) Patent No.: US 7,049,073 B2
(45) Date of Patent: May 23, 2006

(54) DOUBLE STRANDED NUCLEIC ACID BIOCHIPS

(75) Inventors: Boris Chernov, Willowbrook, IL (US); Julia Golova, Willowbrook, IL (US)

(73) Assignee: The University of Chicago, Chicago, IL (US)

( * ) Notice: Subject to any disclaimer, the term of this patent is extended or adjusted under 35 U.S.C. 154(b) by 103 days.

(21) Appl. No.: 10/283,670

(22) Filed: Oct. 30, 2002

(65) Prior Publication Data

US 2004/0086866 A1 May 6, 2004

(51) Int. Cl.
C12Q 1/68 (2006.01)
G01N 33/543 (2006.01)
G01N 33/554 (2006.01)

(52) U.S. Cl. .......... 435/6; 435/DIG. 42; 435/DIG. 40; 435/DIG. 34; 435/DIG. 37; 435/DIG. 2; 435/DIG. 14; 435/DIG. 17; 435/174; 435/180; 436/518; 436/528; 436/529; 536/23.1; 536/25.3; 549/223; 549/227

(58) Field of Classification Search ............... 536/23.1, 536/25.3, 25.32; 546/25, 102; 549/223, 549/227; 435/6, DIG. 2, DIG. 34, DIG. 40, 435/DIG. 42; 436/518, 528, 529
See application file for complete search history.

(56) References Cited

U.S. PATENT DOCUMENTS

| | | | |
|---|---|---|---|
| 5,905,024 | A | 5/1999 | Mirzabekov et al. |
| 5,981,734 | A | 11/1999 | Mirzabekov et al. |
| 6,056,859 | A | 5/2000 | Ramsey et al. |
| 6,087,102 | A | 7/2000 | Chenchik et al. |
| 6,143,499 | A | 11/2000 | Mirzabekov et al. |
| 6,187,913 | B1 * | 2/2001 | Blumenfeld et al. ....... 536/23.1 |
| 6,190,889 | B1 | 2/2001 | Jones |
| 6,203,683 | B1 | 3/2001 | Austin et al. |
| 6,238,868 | B1 | 5/2001 | Carrino et al. |
| 6,242,246 | B1 | 6/2001 | Gold et al. |
| 6,258,533 | B1 | 7/2001 | Jones |
| 6,287,768 | B1 | 9/2001 | Chenchik et al. |
| 6,309,833 | B1 | 10/2001 | Edman et al. |
| 6,326,173 | B1 | 12/2001 | Edman et al. |
| 6,376,181 | B1 | 4/2002 | Ramsey et al. |
| 6,403,338 | B1 | 6/2002 | Knapp et al. |
| 6,406,893 | B1 | 6/2002 | Knapp et al. |
| 6,410,668 | B1 | 6/2002 | Chiari et al. |
| 2001/0006785 | A1 | 7/2001 | Ramsey et al. |
| 2002/0012902 | A1 | 1/2002 | Fuchs et al. |
| 2002/0055187 | A1 | 5/2002 | Treptow |
| 2002/0068334 | A1 | 6/2002 | Carrino et al. |
| 2002/0072055 | A1 | 6/2002 | Jones |
| 2002/0095073 | A1 | 7/2002 | Jacobs et al. |

FOREIGN PATENT DOCUMENTS

| | | |
|---|---|---|
| WO | WO 98/2844 | 7/1998 |
| WO | WO 99/27140 | 6/1999 |
| WO | WO 00/52208 A3 | 9/2000 |
| WO | WO 00/65098 | 11/2000 |
| WO | WO 01/14437 A1 | 3/2001 |
| WO | WO 02/27312 A1 | 4/2002 |
| WO | WO 02/42775 A2 | 5/2002 |

OTHER PUBLICATIONS

Braun, Erez, et al. (1998) "DNA-templated Assembly and Electrode Attachment of a Conducting Silver Wire" *Letters to Nature* 391:775-778.

Brockman, Jennifer M., et al. (1999) "A Multistep Chemical Modification Procedure to Create DNA Arrays on Gold Surfaces for the Study of Protein—DNA Interactions with Surface Plasmon Resonance Imaging" *J. Am. Chem. Soc.* 121:8044-8051.

Broude, Natalia E., (2001) "DNA Microarrays with Stem-Loop DNA Probes: Preparation and Applications" *Nucleic Acids Research* 29: No. 19 e92: 1-11.

Bulyk, Martha L., et al. (1999) "Quantifying DNA-Protein Interactions by Double-Stranded DNA Arrays" *Nature Biotechnology* 17:573-577.

Carlson, Robert and Brent, Roger (1999) "Double-Stranded DNA Arrays: Next Steps in the Surface Campaign" *Nature Biotechnology* 17:536-537.

Carmon, A., et al., (2002) "Solid-Phase PCR in Microwells: Effects of Linker Length and Composition on Tethering, Hybridization, and Extension" *BioTechniques* 32:2: 410-420.

Jackson, Nicole M. and Hill, Michael G. (2001) "Electrochemistry at DNA-Modified Surfaces: New Probes for Charge Transport Through the Double Helix" *Current Opinion in Chemical Biology* 5:209-215.

O'Brien, Janese C., et al. (2000) "Preparation and Charaterization of Self-Assembled Double-Stranded DNA (dsDNA) microarrays for Protein:dsDNA Screening Using Atomic Force Microscopy" *Langmuir* 16:9559-9567.

Riccelli, P.V., et. al. (2001) "Hybridization of Single-Stranded DNA Targets to Immobilized Complementary DNA Probes: Comparison of Hairpin Versus Linear Capture Probes" *Nucleic Acids Research* 29:4:996-1004.

(Continued)

*Primary Examiner*—Padmashri Ponnaluri
*Assistant Examiner*—My-Chau T. Tran
(74) *Attorney, Agent, or Firm*—Alice O. Martin; Barnes & Thornburg LLP

(57) ABSTRACT

This invention describes a new method of constructing double-stranded DNA (dsDNA) microarrays based on the use of pre-synthesized or natural DNA duplexes without a stem-loop structure. The complementary oligonucleotide chains are bonded together by a novel connector that includes a linker for immobilization on a matrix. A non-enzymatic method for synthesizing double-stranded nucleic acids with this novel connector enables the construction of inexpensive and robust dsDNA/dsRNA microarrays. DNA-DNA and DNA-protein interactions are investigated using the microarrays.

21 Claims, 16 Drawing Sheets

OTHER PUBLICATIONS

Sam, Mui, et. al. (2001) "Morphology of 15-mer Duplexes Tethered to Au(111) Probed Using Scanning Probe Microscopy" *Langmuir* 17:5727-5730.

Shchyolkina, Anna K., et. al. (2000) "Parallel-Stranded DNA with Mixed AT/GC Composition: Role of Trans G·C Base Pairs in Sequence Dependent Helical Stability" *Biochemistry* 39:33;10034-10044.

Sinha, N.D., et. al. (1983) "β-Cyanoethyl N, N-Dialkylamino/N-Morpholinomonochloro Phosphoamidites, New Phosphitylating Agents Facilitating Ease of Deprotection and Work-up of Synthesized Oligonucleotides" *Tetrahedron* 24:52:5843-5846.

Tchurikov, Nickolai, A., et. al. (1989) "Parallel DNA: Generation of a Duplex Between Two Drosophila Sequences" *FEBS Letters* 257:2:415-418.

Yan, Fei and Sadik, Omowunmi A. (2001) "Enzyme-Modulated Cleavage of dsDNA for Supramolecular Design of Biosensors" *Anal. Chem.* 73:5272-5280.

Zhao, Xiaodong, et. al. (2001) "Immobilization of Oilgodeoxyribonucleotides with Multiple Anchors to Microchips" *Nucleic Acids Research* 29:4:955-959.

M.S. Shchepinov, S.C. Case-Green and E.M. Southern, Steric Factors Influencing Hybridisation of Nucleic Acids to Oligonucleotide Arrays, *Nucleic Acids Research*, 1997, vol. 25, No. 6, pp. 1155-1161.

\* cited by examiner

Scheme 1

The strategy of synthesis of connector phosphoramidite (7)

Reagents: a) Ethyl trifluoroacetate
b) N,N-Dicyclohexylcarbodiimide/N-Hydroxysuccinimide
c) 4,4'-Dimethoxytrityl chloride
d) Methylamine
e) 2-Cyanoethyl diisopropylchlorophosphoramidite/
N,N-Diisopropylethylamine

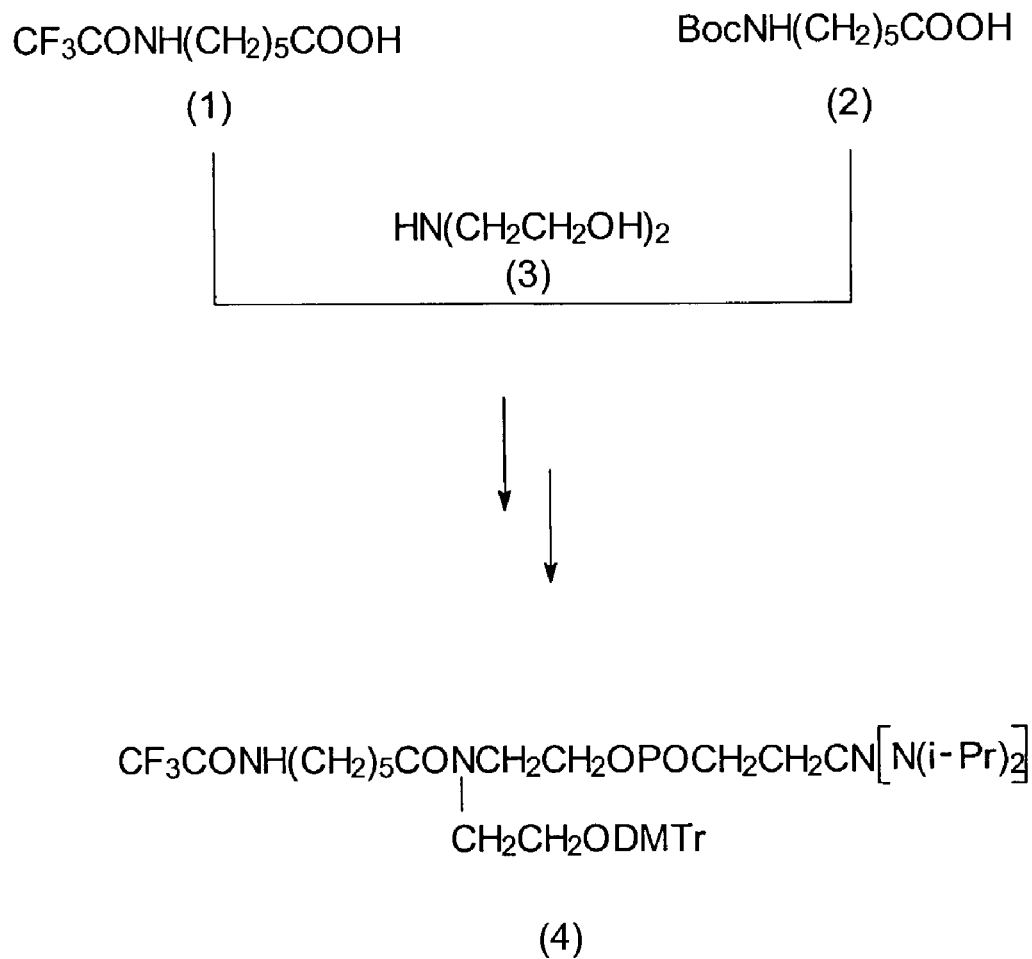
Scheme 2
Preparation of connector phosphoramidite (4)

1. L —TT GCGCTCGAGGCC
      TT CGCGAGCTCCGG (SEQ ID NO: 3)   L - Connector
         Cfol    HaeIII
                  Xhol 2. L —TTTT GCGCTCGAGGCC
      TTTT CGCGAGCTCCGG (SEQ ID NO: 4)
         Cfol    HaeIII
                  Xhol 3. L —TTTT GCGCTCGAGGCC
      TTTT CGCGAGCTCCGG-NH-FITC (SEQ ID NO: 5)   FITC - fluorescent label
         Cfol    HaeIII
                  Xhol 4. L —TT(A)$_n$AAGCTTCGAATTCGA GG
      TT(T)$_n$TTCGAAGCTTAAGCT CC (SEQ ID NO: 6)   n=4
         HindIII  EcoRI
         Csp    TagI 5. L —TT(A)$_n$AAGCTTCGAATTCGA GG
      TT(T)$_n$TTCGAAGCTTAAGCT CC-NH-FITC   FITC - fluorescent label
         HindIII  EcoRI           n=4
         Csp    TagI   (SEQ ID NO: 7)

Scheme 3

FIG. 6 cont.

1.  L⌐ T T C TATCACCGCCAGAGGTA GC 3'  
        T T G ATAGTGGCGGTCTCCAT CG 5'  OR (var.1)  
    (SEQ ID NO: 8)

L - Connector

2.  L⌐ T T A$_n$TATCACCGCCAGAGGTA GC 3'  
        T T T$_n$ATAGTGGCGGTCTCCAT CG 5'  OR (var.2)  
    (SEQ ID NO: 9)

n=4

3.  L⌐ T T C TTCCGAACGCAAGCTCA GC 3'  
        T T G AAGGCTTGCGTTCGAGT CG 5'  Antisense I  
    (SEQ ID NO: 10)

4.  L⌐ T T A$_n$TTCCGAACGCAAGCTCA GC 3'  
        T T T$_n$AAGGCTTGCGTTCGAGT CG 5'  Antisense II  
    (SEQ ID NO: 11)

n=4

Scheme 4

Connector phosphoramidite L

B

C Possible structures of synthetic DNA duplexes ds DNA probe

+

MATRIX:

1. Polyacryamide gel pads
2. Hydro-gels
3. Glass surface (slides, beads)
4. Silicon surface
5. Gold surface (slides, beads)
6. Magnetic beads covered by latex containing carboxylic groups (COOH)

A. UV-Spectrum of the Duplex 4 (Scheme 3, Fig.6 cont),
   Abs – absorbtion, λ – wave length B. Melting curve of the Duplex 4 (Scheme 3, Fig.6 cont)
   ABS- absorbtion, t oC – temperature in Celsius MATRIX:
1) Hydro-gels
2) Glass surface
3) Silicon surface
4) Gold surface
5) Magnetic beads

SUBSTRATE:

ds DNA duplex

1.

2.

3.

4.

5.

SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 1
cccctttttt tcgaattcct tttccc                                          26

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 2
cctggaaaaa accagggtat tcttataact gac                                  33

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Between positions 13 & 14 there is a
      non-nucleotide phosphoramidite L-connector

<400> SEQUENCE: 3
ccggagctcg cgttttcgcg agctccgg                                        28

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primer

```
<220> FEATURE:
<223> OTHER INFORMATION: Between positions 16 & 17 there is a
      non-nucleotide phosphoramidite L-connector

<400> SEQUENCE: 4
ccggagctcg cgttttttttt cgcgagctcc gg                               32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Between positions 16 & 17 there is a
      non-nucleotide phosphoramidite L-connector and on the 3' end there
      is a fluorescent label

<400> SEQUENCE: 5
ccggagctcg cgttttttttt cgcgagctcc gg                               32

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Between positions 23 & 44 there is a
      non-nucleotide phosphoramidite L-connector

<400> SEQUENCE: 6
ggagcttaag cttcgaaaaa attttttttc gaagcttaag ctcc                   44

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Between positions 23 & 24 there is a
      non-nucleotide phosphoramidite L-connector and on the 3' end there
      is a fluorescent label

<400> SEQUENCE: 7
ggagcttaag cttcgaaaaa attttttttc gaagcttaag ctcc                   44

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Between positions 22 & 23 there is a
      non-nucleotide phosphoramidite L-connector

<400> SEQUENCE: 8
gctacctctg gcggtgatag ttttctatca ccgccagagg tagc                   44

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Primer
```

```
<220> FEATURE:
<223> OTHER INFORMATION: Between positions 24 & 25 there is a
      non-nucleotide phosphoramidite L-connector

<400> SEQUENCE: 9
gctacctctg gcggtgatat tttttttaaa atatcaccgc cagaggtagc            50

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Between positions 22 & 23 there is a
      non-nucleotide phosphoramidite L-connector

<400> SEQUENCE: 10
gctgagcttg cgttcggaag ttttcttccg aacgcaagct cagc                  44

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Between positions 24 & 25 there is a
      non-nucleotide phosphoramidite L-connector

<400> SEQUENCE: 11
gctgagcttg cgttcggaat tttttttaaa attccgaacg caagctcagc            50

<210> SEQ ID NO 12
<211> LENGTH: 42
<212> TYPE: DNA
<213> ORGANISM: Artificial Sequence
<220> FEATURE:
<221> NAME/KEY: modified_base
<222> LOCATION: (1)..(3)
<223> OTHER INFORMATION: a, t, c, g, other or unknown
<220> FEATURE:
<221> NAME/KEY: modified_base
<222> LOCATION: (10)..(12)
<223> OTHER INFORMATION: a, t, c, g, other or unknown
<220> FEATURE:
<221> NAME/KEY: modified_base
<222> LOCATION: (19)..(24)
<223> OTHER INFORMATION: a, t, c, g, other or unknown
<220> FEATURE:
<221> NAME/KEY: modified_base
<222> LOCATION: (31)..(33)
<223> OTHER INFORMATION: a, t, c, g, other or unknown
<220> FEATURE:
<221> NAME/KEY: modified_base
<222> LOCATION: (40)..(42)
<223> OTHER INFORMATION: a, t, c, g, other or unknown
<220> FEATURE:
<223> OTHER INFORMATION: Description of Artificial Sequence: Primer

<400> SEQUENCE: 12
nnnttcgaan nncctaggnn nnnncctagg nnnttcgaan nn                    42

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer
```

```
<220> FEATURE:
<221> NAME/KEY: modified_base
<222> LOCATION: (2)..(4)
<223> OTHER INFORMATION: a, t, c, g, other or unknown
<220> FEATURE:
<221> NAME/KEY: modified_base
<222> LOCATION: (11)..(16)
<223> OTHER INFORMATION: a, t, c, g, other or unknown
<220> FEATURE:
<221> NAME/KEY: modified_base
<222> LOCATION: (23)..(25)
<223> OTHER INFORMATION: a, t, c, g, other or unknown

<400> SEQUENCE: 13
annncctagg nnnnnnccta ggnnnttcga                              30

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (7)..(9)
<223> OTHER INFORMATION: a, t, c, g, other or unknown
<220> FEATURE:
<221> NAME/KEY: modified_base
<222> LOCATION: (16)..(21)
<223> OTHER INFORMATION: a, t, c, g, other or unknown
<220> FEATURE:
<221> NAME/KEY: modified_base
<222> LOCATION: (28)..(30)
<223> OTHER INFORMATION: a, t, c, g, other or unknown

<400> SEQUENCE: 14
ttcgaannnc ctaggnnnnn ncctaggnnn ttcgaa                       36

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(4)
<223> OTHER INFORMATION: a, t, c, g, other or unknown
<220> FEATURE:
<221> NAME/KEY: modified_base
<222> LOCATION: (22)..(29)
<223> OTHER INFORMATION: a, t, c, g, other or unknown
<220> FEATURE:
<221> NAME/KEY: modified_base
<222> LOCATION: (47)..(50)
<223> OTHER INFORMATION: a, t, c, g, other or unknown

<400> SEQUENCE: 15
nnnnatggag accgccacta tnnnnnnnna tagtggcggt ctccatnnnn        50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(4)
<223> OTHER INFORMATION: a, t, c, g, other or unknown
```

```
-continued
<220> FEATURE:
<221> NAME/KEY: modified_base
<222> LOCATION: (22)..(29)
<223> OTHER INFORMATION: a, t, c, g, other or unknown
<220> FEATURE:
<221> NAME/KEY: modified_base
<222> LOCATION: (47)..(50)
<223> OTHER INFORMATION: a, t, c, g, other or unknown

<400> SEQUENCE: 16
nnnnatggag accgccacta tnnnnnnnna tagtggcggt ctccatnnnn          50
```

DOUBLE STRANDED NUCLEIC ACID BIOCHIPS

The United States Government has rights in this invention under Contract No. W-31-109-ENG-38 between the U.S. Department of Energy (DOE) and the University of Chicago representing Argonne National Laboratory.

BACKGROUND

Methods and compositions for preparation of double stranded nucleic acid molecules, e.g. dsDNA, by novel connectors that include linkers that attach the molecules to a matrix, are useful for the investigation of protein-nucleic acid interactions and nucleic acid structure.

Single-stranded DNA (ssDNA) microarrays have been extensively reported and used to screen genetic polymorphisms, mutations and gene expression to answer various questions. However, analysis of genetic transcription, replication, and restriction enzyme engineering requires dsDNA microarrays.

During the past several years many developments were reported in DNA microarray (biochip)-based automated technology that allowed parallel analysis of multiple DNA samples. Most of these biochips are based on application of single stranded DNA (ssDNA) microarrays, which are used in hybridization experiments with different kinds of DNA samples. Single-stranded DNA biochips are reported for gene expression profiling, gene polymorphism analysis, and mutation screening.

However, many important investigations in molecular biology cannot be served by this format of DNA microarrays. For example, systematic investigation of DNA-protein interactions which includes investigation of recombination, transcription, replication, and also discovery and engineering of new restriction enzymes, requires double stranded DNA microarrays.

There are many different approaches to the creation of double stranded DNA (dsDNA) microarrays. Different supports, linkers, base pair lengths, and types of DNA are reported for various applications.

A brief review of the major work and achievements in dsDNA biochip manufacturing is as follows:

There were two main approaches to construct dsDNA arrays. In the first, a single oligonucleotide strand was attached to a matrix, and then duplexes were formed by hybridization of the attached strand with complementary chains. The second method is based on manufacturing dsDNA arrays by using hairpin stem-loop DNA molecules attached to the matrix across the loop-part and hybridized to form only a partial duplex structure. The full duplex can be obtained by using enzyme polymerase if needed.

A method used for fabrication of dsDNA microarrays on a glass surface is illustrated in FIG. 1 (Bulyk, 1999). In the first step of creation of dsDNA arrays, single stranded DNA probes are synthesized on a glass surface by light-directed methods of oligonucleotide synthesis. Unfortunately, the efficiency of this method of synthesis is not high—92–94% per one step of oligonucleotide synthesis, thus for a 40-mer oligonucleotide, only from 5 to 20% of the synthesized oligonucleotides on the glass surface will be of the desired length and sequence (Carlson, 1999). Short synthetic primers are then annealed to the single stranded oliogonucleotide probes on the glass surface. Finally, the full duplex is obtained by Klenow polymerase reaction. The labeling of dsDNA probes thus created is carried out by fluorescein labeled dNTPs during a polymerization reaction, or by use of terminal transferase addition of fluorescein-labeled ddNTPs. However, this method is very time consuming and it is impossible to guarantee the high precision of answers using these microarrays.

Another approach to manufacturing dsDNA arrays is shown in FIG. 2. In this method (Braun, 1998) the first step uses the same light-directed oligonucleotide synthesis as in FIG. 1 on a glass or gold surface e.g. a microscope "slide." Then, double stranded DNA fragments with protruding ends (complementary to probes attached to the chip) are hybridized to the immobilized oligonucleotides. The treatment of the resulting complex with DNA ligase creates a surface coupled dsDNA microarray. However, all disadvantages of the previously described method are present here too.

Another way for obtaining dsDNA arrays was demonstrated by O'Brien and coworkers (see FIG. 3). The authors made dsDNA microarrays for protein—dsDNA screening and investigation of antigen-antibody binding using Atomic Force Microscopy. First, the set of complementary oligonucleotide pairs was synthesized by means of a standard solid phase approach using phosphoramidite chemistry (Sinha, 1983). Then, self-assembled DNA duplexes with recognition sites for the EcoRI restriction endonuclease and fluorescein moieties above the recognition sequences were obtained by annealing complementary chains in solutions before the creation of microarrays. Each of the complementary oligonucleotides contained a disulfide moiety, which provided further bonding of the duplexes to the surface of slide. However, the authors emphasized that there were serious problems with the standardization of capacity parameters of microarrays in that method. Also the high level of nonspecific adsorption of DNA probes can dramatically affect further experiments with this chip and interpretation of obtained results.

Other methods created DNA microarrays with hairpin structured probes (see FIG. 4A, Zhao et al., 2001). One method was based on the covalent attachment of the hairpin stem-loop structure to a matrix. In this work oligonucleotides with five phosphorothioate residues in the loop were synthesized. The presence of these multiple phosphorothioate functions in the hairpin structure was used to anchor the oligonucleotide to a glass slide surface. A problem was that covalent attachment to the slide may occur statistically in every position of the loop, so geometric parameters of the hairpin can vary and as a result, can influence the formation of correct duplexes, especially for short complements (e.g. 5 base pairs). Then, complete labeled duplexes were obtained by extension of hairpin structures on a glass slide by use of T7 sequenase in the presence of cyanine dye labeled ddGTP (see FIG. 4B)

The paper of Riccelli and coworkers (see FIG. 5A) reported the use of hairpin probes made from a partial duplex (16 base pairs and a 32-base long single strand end) and a loop with biotinylated uracil as a linker in the middle. By this linker the structure was coupled to avidin coated microtiter wells. It was reported that such hairpin DNA probes attached to the chip displayed higher rates of hybridization and larger equilibrium amounts of captured targets in comparison with linear probes. Also, hairpin DNA—target complexes were thermodynamically more stable.

DNA microarrays containing stem-loop DNA probes with short single-stranded overhangs were immobilized on 3-dimensional Packard HydroGel chips by Broude et al. (2001). Microarrays were fabricated by immobilizing pre-synthesized, self-complementary single-stranded oligonucleotides which adopt partially duplex dsDNA was then biotinylated at single stranded regions. The biotinylated dsDNA was then used as a ligand at a gold electrode covered by avidin. The obtained biosensors were said to be useful to determine small molecular weight organics, that is, a dsDNA based sensor, and for monitoring DNA-analyte interactions.

Although much effort has been expended in this research area, improvements are needed so that dsDNA microchips can be manufactured efficiently and used effectively.

SUMMARY OF THE INVENTION

This invention describes novel methods and compositions to create double-stranded nucleic acid, e.g. DNA (dsDNA) microarrays. Nucleic acid duplexes are synthesized to include connectors and linkers, and methods for immobilization of the dsDNA to biochips is by novel connectors that include linkers.

The resulting DNA duplexes do not have the cumbersome loops at the point of connection of complementary chains characteristic of some DNA duplexes synthesized in the art and their construction does not require enzymes. DNA-DNA, RNA-RNA, DNA-RNA, RNA-protein and DNA-protein interactions are investigated using the biochips.

A method for creating dsDNA biochips (microarrays) includes the steps of:
1. synthesizing at least one DNA duplex in which complementary oligonucleotude chains are covalently joined together by a novel connector;
2. attaching the synthesized DNA duplexes to a matrix to form a biochip (microarray) by free amino-groups of linkers incorporated into the connector.

The connector is a bifunctional molecule that can be placed between the two complementary nucleotide chains, which causes the respective strands on each side of the connector to hybridize without a loop formation. The smaller size of the attachment region facilitates the incorporation of more DNA duplexes to the same area of the matrix than would be possible using a stem loop structure. Additionally, this synthesis method does not involve enzymatic reactions, which tend to be more stem-loop structures upon denaturing and re-annealing. Stem-loop DNA probes were covalently attached to the matrix by modified nucleosides incorporated in the middle of the loop. The structure obtained was used in hybridization experiments followed by ligase reaction, and the results in searching and analysis of single nucleotide polymorphisms in the p53 gene were reported as good (FIG. 5B).

Another approach for making dDNA microarrays was to use thiol-derivatized 15 base pair duplexes tethered through single 3' and 5' linkages to a gold [Au(III)] surface. The long-range film structure was measured by scanning probe microscopy. These microarrays are designed for use in nanotechnology or as biosensors. One conclusion of this study was that placement and composition of linkers will affect the film structure of DNA microarrays e.g. 3' duplex linkage results in a flat surface, also linker length and composition may induce different chain-duplex interactions and possibly duplex self-assembly (Sam et al., 2001). Therefore, different tethering methods likely result in different dsDNA microarrays.

Brockman et al. (1999) related a chemical modification procedure to create DNA arrays on gold surfaces for the study of protein-DNA interactions. Surface plasma resonance (SPR) imaging was used. The authors noted that "DNA arrays on glass supports from commercially available sources such as Affymetrix[13] are not a viable option" for SPR imaging investigations of protein-DNA binding interactions (p. 8045, col. 1), because this method needs to use DNA arrays on the metal surface. The authors investigated the binding of proteins that are specifically bonded with single-stranded DNA. Both single and double stranded DNA were spotted in a microarray. It was shown, that these proteins bound to single stranded DNA, but only very little bound to dsDNA.

Some goals of microarray DNA molecules, single or double stranded, immobilized on solid supports, are to use DNA chips as films for, e.g. electric charge transport. Jackson and Hill (2001) studied a charge transport through DNA double helices. The presynthesized duplexes were self-assembled onto gold surface, and the resulting films have been characterized by electrochemistry.

For the development of biosensors dsDNA was immobilized on self-assembled avidin monolayer onto a metal surface (Yan and Sadik, 2001). Circular plasmid dsDNA was linearized using the restriction endonuclease BamHI. The expensive and less efficient than the present methods. Additionally, dsDNA molecules without a loop structure are preferred for interaction with target substances.

A method of investigating dsDNA-protein interactions includes the following steps:
1. synthesizing at least one dsDNA probe with a specific nucleotide sequence and a connector that forms a DNA duplex;
2. attaching the synthesized DNA duplex to a matrix to form a biochip;
3. providing conditions for individual peptide targets to interact with specific dsDNA probes on the biochip; and
4. measuring parameters from which the dsDNA-protein interactions are inferred.

A method for designing a dsDNA biochip by using dsDNA specific enzymes such as restriction endonucleases and ligases, includes the following steps:
1. synthesizing at least one dsDNA probe with a specific nucleotide sequence and containing at least one site for restriction endonuclease recognition, and a connector to form a duplex;
2. attaching the synthesized DNA duplex to a matrix to form a biochip;
3. digesting the DNA duplexes on the biochip with site specific restriction enzymes to create dsDNA probes with protruding ends;
4. annealing the dsDNA probes on the biochip with dsDNA fragments containing complementary protruding ends; and
5. ligating annealed dsDNA fragments at the restricted point.

A method of chemical synthesis of specific connector phosphoramidite L (7) of the present invention is shown in FIG. 6, Scheme 1.

An aspect of the invention is a microchip with dsDNA oligonucleotides each anchored to gel pads on the surface of the microchip by the linkers of the present invention.

An aspect of the invention is a connector characterized as a bifunctional phosphoramidite L (FIG. 7A) wherein the connector contains a linker with free amino-groups for immobilization on a biochip matrix (FIG. 7B).

A composition of the present invention is a connector constructed by Scheme 1 of FIG. 6. An $NH_2$-group of aminoacid 1 was blocked by reaction of ethyltrifluoroacetate in methanol (1→2). Then a carboxylic group in 2 was converted in activated ester 3 by reaction with N-hydroxysuccinimide and N,N-dicyclohexylcarbodiimide. To obtain compound 5 a one-flask method of synthesis was used. It included sequential reactions of serinol 4 with ethyl trifluoroacetate 4a and 4,4'-dimethoxytritylchloride followed by treatment of methylamine 4d. Condensation of substances 3 and 4 leads to formation of synthone 6, which gives connector phosphoramidite 7 after phosphorylation by using 2-cyanoethyl diisopropylchlorophosphoramidite. An embodiment of a connector is shown in FIG. 6.

dsDNA probes for biochip manufacturing (FIG. 7C) are synthesized by using a connector phosphoramidite and standard phosphoramidites, and may be a full duplex. Also alternatives to a full duplex can be synthesized, which include a partial duplex with a 3'-protruding end, and a partial duplex with a 5'-protruding end.

Connector phosphoramidite (7) [FIG. 6, Scheme 1] also can be used in standard procedures for oligoribonucleotide synthesis to obtain RNA or RNA-DNA duplexes. The connector phosphoramidite on FIG. 6, Scheme 1=connector phosphoramidite L on FIG. 7A An aspect of the invention is a method of attachment of dsDNA probes including a connector to a biochip (microarray) matrix, which contains active functional groups able to react with amino-groups in connector construction. Novel in this procedure is using dsDNA probes, with the special structure.

Definitions and Abbreviations

Matrix=support (glass slide, gold slide, gel pad, others) on which an array (microarray) of molecules is formed; contains functional groups.

Array, microarray=molecules connected to the matrix in a specific arrangement relative to each other.

Biochip (DNA chip, DNA microarray, DNA array, peptide chip, peptide array and so on)=array of biological molecules e.g. bioprobes (DNA fragments, peptides, others) connected to the matrix in a specific arrangement to each other and designed to answer a specific question.

Bioprobe=molecule which can be used to identify or characterize another molecule e.g. by hybridizing.

Connector=a novel molecule linking together complementary oligonucleotide chains of a DNA/DNA, DNA/RNA or RNA/RNA duplex.

DMTr=dimethoxytrityl.

Linker=a structural element of a connector providing connection of a DNA-duplex to functional groups of a matrix.

MALDI=MS=matrix assisted laser desorption ionization mass spectroscopy.

HEG=hexaethylene glycol.

dNTP=deoxynucleoside triphosphate.

ddNTP=dideoxynucleoside triphosphate.

CY5-ddGTP=cyanine-labeled dideoxeriboguanosinetriphosphate.

FG=functional group.

FZ=Fluorescent Label

PAAG=polyacrylamide gel.

DNA=deoxyribonucleic acid.

RNA=ribonucleic acid.

UV=ultraviolet.

NMR=Nuclear Magnetic Resonance.

Phosphoramidite=building blocks for chemical synthesis of oligodeoxyribonucleotides by phosphoramidite method.

Methods and compositions described herein that relate to dsDNA also include DNA/RNA and RNA/RNA duplexes.

(B) shows a scheme for chemical synthesis of a DNA duplex by using commercial phosphoramidites and connector phosphoramidite L; (C) shows possible structures of synthetic DNA duplexes.

Figure 8:
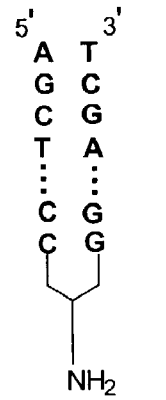
Figure 8:
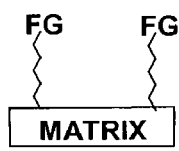
Figure 8:
Figure 8:
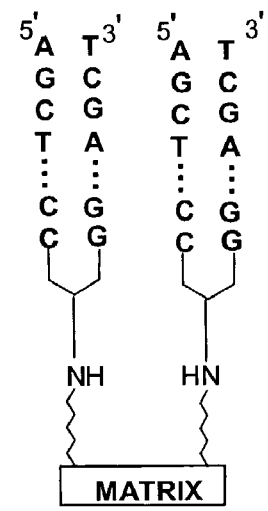

FIG. 8 is a schematic illustration of biochip formation by immobilization of a DNA duplex on a matrix. Six types of matrices are exemplified.

Figure 9:
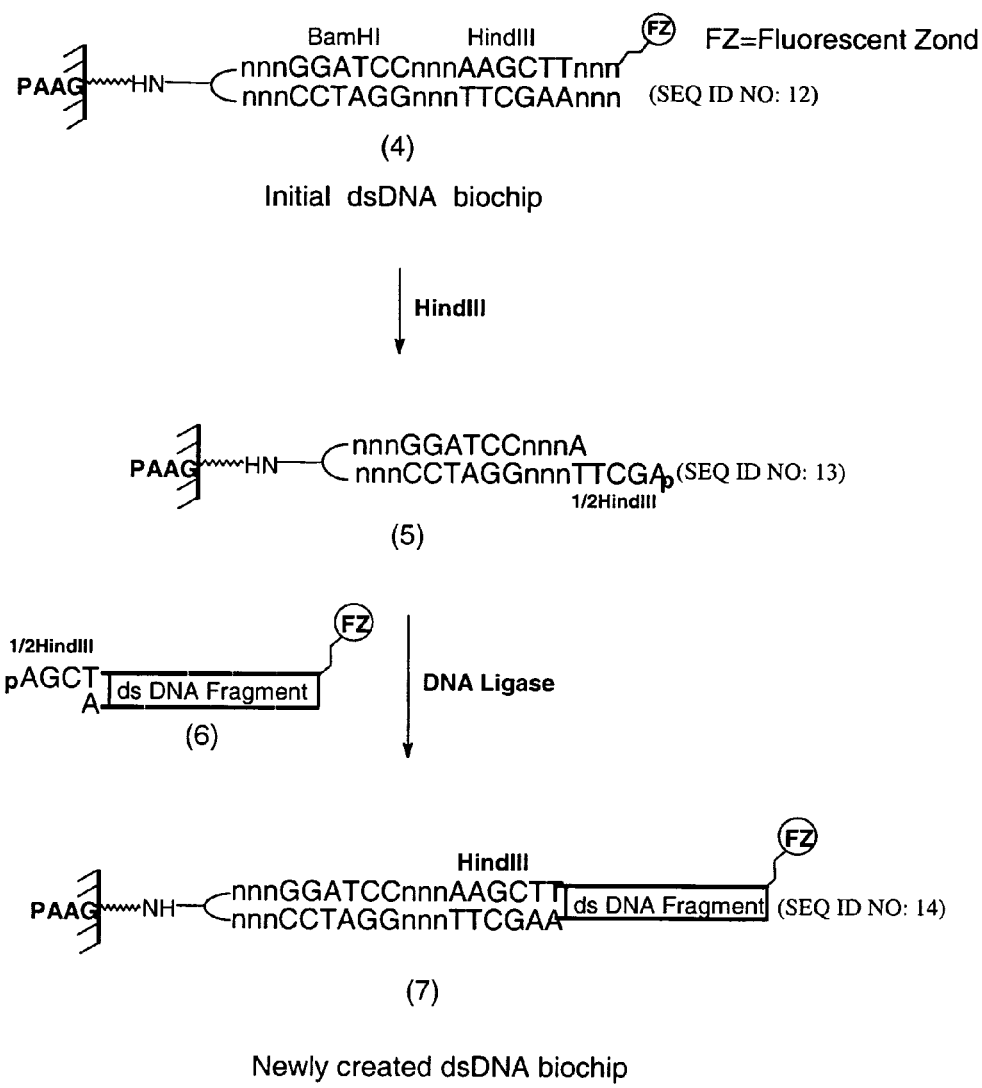

FIG. 9 shows a scheme for creation of a new format for dsDNA-biochips (SEQ ID NOS 12–14, respectively, in order of appearance) by use of enzymatic reactions (restriction endonuclease HindIII and DNA ligase). ½ HindIII is an abbreviation that means half-site of HindIII with protruding ends which appears after digestion of the recognition site with HindIII restriction endonuclease.

Figure 10:
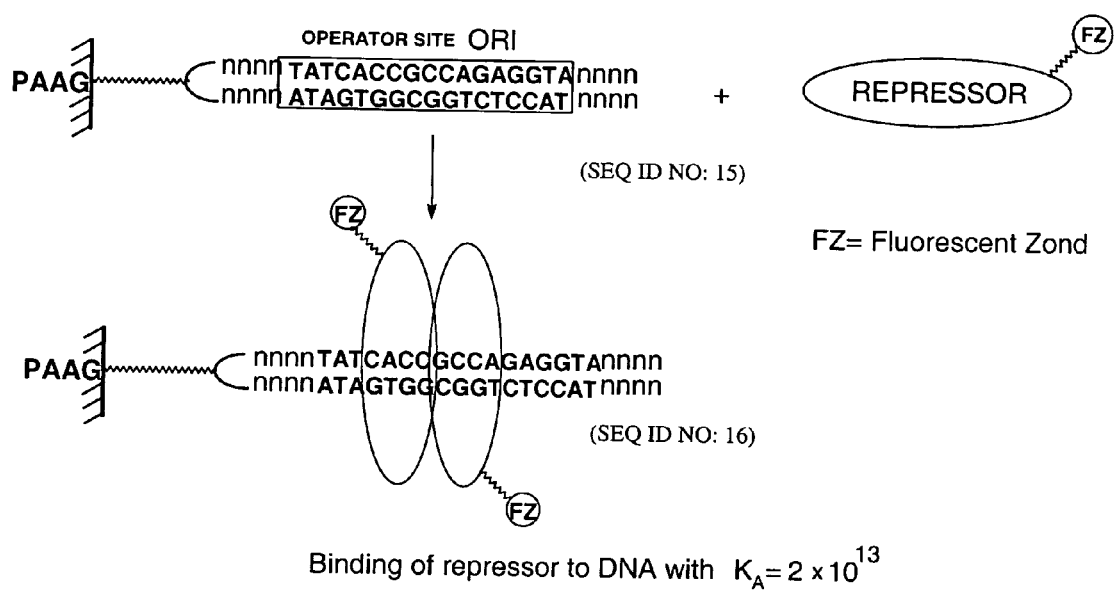

FIG. 10 shows the binding or Lamda Cro-repressor with operator site ORI as a model for investigation of dsDNA-protein interactions by use of a dsDNA-biochip (SEQ ID NOS 15 & 16, respectively, in order of appearance).

Figure 11:
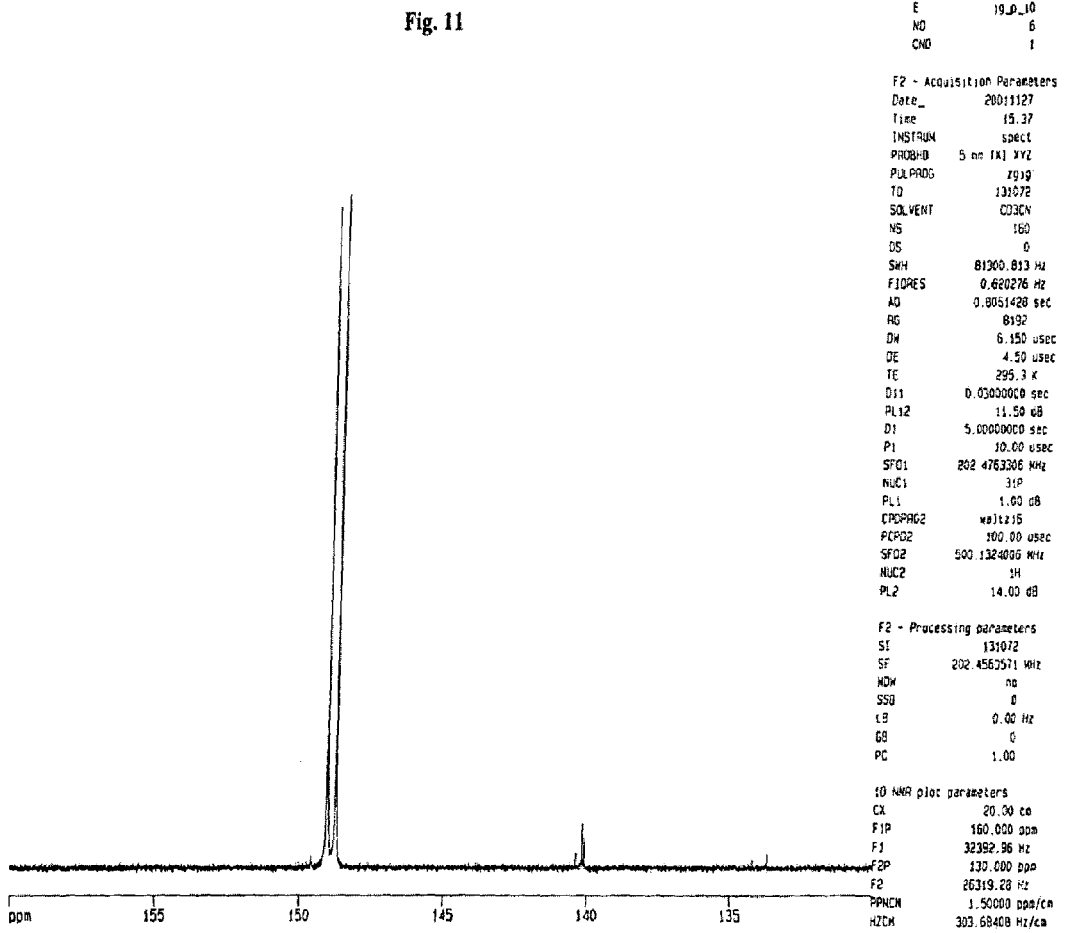

FIG. 11 shows the $P_{31}$NMR Spectrum of connector phosphoramidite 7.

Figure 6:
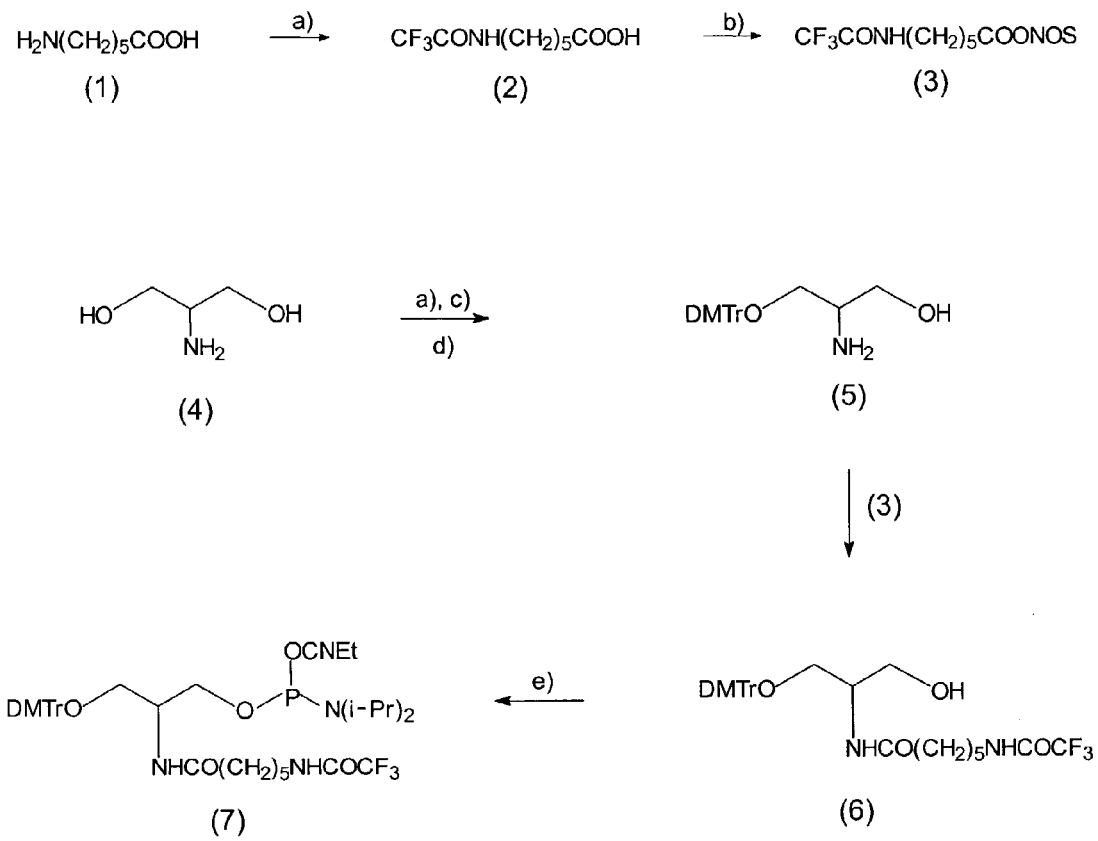
FIG. 6, Scheme 1 shows the synthesis strategy for a connector phosphoramidite (7) of the present invention. Scheme 2 shows the synthetic way for preparation of connector phosphoramidite (4), an unsuccessful embodiment proposed for a connector structure. Scheme 3 demonstrates the structures of synthesized duplexes (SEQ ID NOS 3–7, respectively, in order of appearance) to be used for the formation of new duplex formats on 3D dsDNA biochips by use of restriction digestion followed by ligase reaction. Scheme 4 shows the structures of DNA duplexes (SEQ ID NOS 8–11, respectively, in order of appearance) containing Lambda Phage operator site ORI and antisense-duplexes useful for investigation of dsDNA-protein interaction on 3D biochips.
Figure 12:
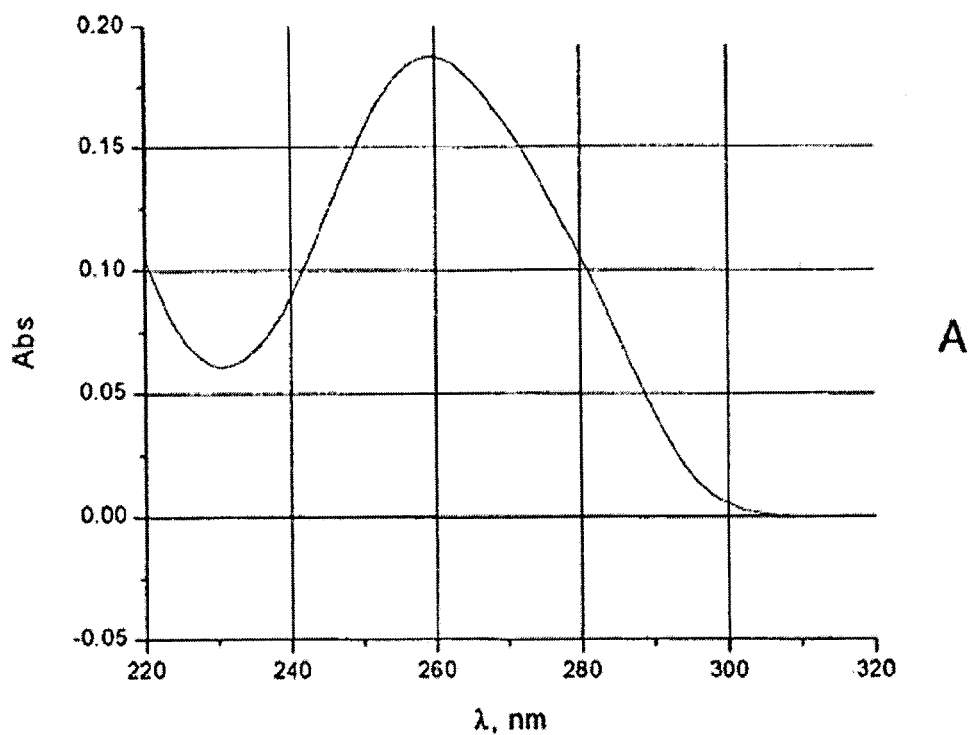
Figure 12:
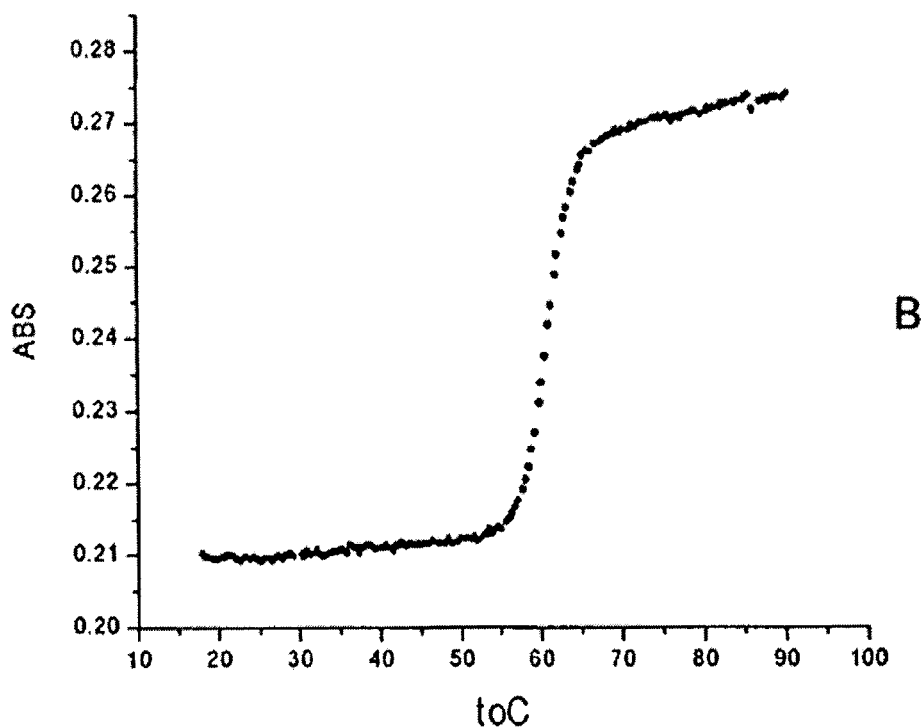

FIG. 12 shows (A) a UV spectrum and (B) melting curve of synthesized DNA duplex 4 (see FIG. 6 cont., Scheme 3).

Figure 13:
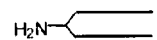
Figure 13:
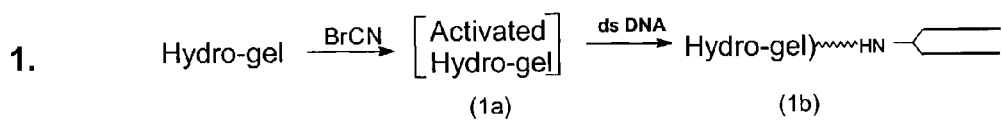
Figure 13:
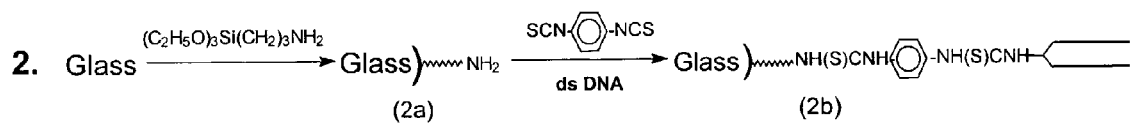
Figure 13:
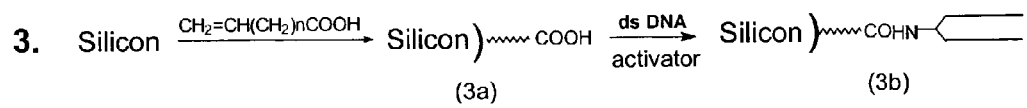
Figure 13:
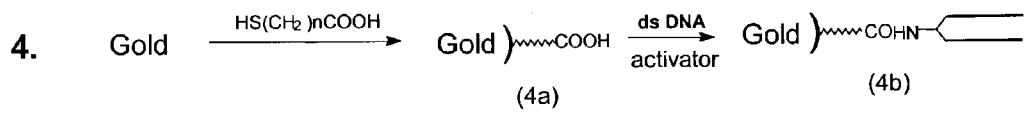
Figure 13:
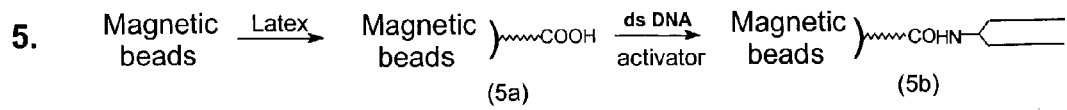

FIG. 13 demonstrates approaches to immobilization of dsDNA probes on different kinds of matrices.

DETAILED DESCRIPTION OF THE INVENTION

The present invention is directed to novel methods and compositions to create and use double stranded DNA microarrays (biochips). dsRNA or RNA/DNA duplexes can be made similarly. Methods are based on use of synthesized DNA duplexes in which complementary chains are covalently bonded by a novel connector including a linker for attachment to a support (matrix). A range of suitable oligonucleotide lengths attached to the connector includes:
  about 10–40 base pairs—for synthesized dsDNA probes; and
  up to about 400 base pairs—for natural dsDNA fragments.

Natural DNA fragments can be obtained from commercial sources or isolated by methods known to those of skill in the art. These can be longer than DNA made synthetically because of technical restrictions on the latter.

The present invention is a new and promising tool for many molecular biological investigations based on DNA-protein interactions, and can also be used for creation of new formats of microarrays including the biochips bearing the fragments of natural DNA (e.g. genomic, bacterial, phage, and the like).

dsDNA microarrays of dsDNA will significantly enhance the performance of nucleic acid assays for known applications such as gene expression profiling, analysis of single nucleotide polymorphism or high-throughput diagnostic and also investigations of DNA-protein interactions. The latter application includes studying fundamental cell processes, such as recombination, transcription, replication in which dsDNA chains are involved. Aspects of experiments based on use of dsDNA-protein interactions include restriction enzyme discovery and engineering. dsDNA arrays also can be useful in design and engineering of new peptide structures to control gene expression in biotechnology applications ranging from functional genomics to gene therapy.

In an embodiment, 3-D Acrylamide Gel Chips created in Argonne National Laboratory are used as matrices for manufacturing 3-dimensional (3D) dsDNA biochips. Other kinds of matrices (such as glass slides or beads, gold slides) are also suitable. A preferred matrix used for manufacturing of dsDNA-biochip contains active functional groups, which are able to react with free amino-functional groups of the connector (FIG. 8).

The fields of application for the double-stranded DNA biochips include:
  High-throughput diagnostics;
  Single-nucleotide polymorphism genotyping;
  Gene expression profiling;
  Investigation of DNA-protein interactions such as: recombination, transcription, replication;
  Discovery and engineering of restriction enzymes;
  Design and engineering of new peptide structures to control gene expression in biotechnology applications.

Design and Chemical Synthesis of a Connector of the Present Invention

General characteristics of a connector include:
  Geometrical parameters and conformational mobility of the connector allows the correct duplex formation.
  Hydrophilic properties are close to properties of the nucleic acids. The molecules of the present invention are soluble in water at the same concentrations as molecules without a connector.

Figure 7:
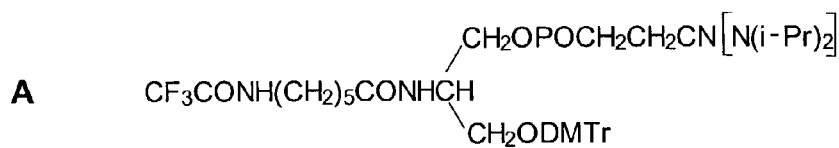
FIG. 7(A) shows a structure of connector phosphoramidite L; oligonucleotides as a sequence of letters "A,C, G and T" which correspond to the nucleotides (adenosine, cytosine, guanosine and thymidine). The letter "L" shows the place where the connector is in the synthesized oligonucleotide chain. This is 7 from Scheme 1, FIG. 6.
Figure 7:
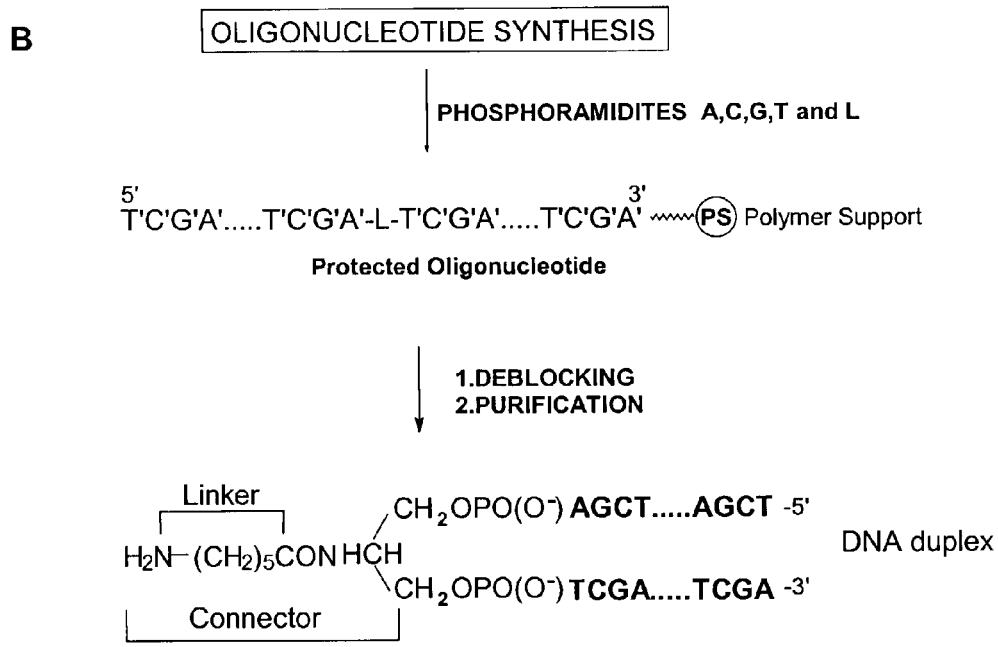
Figure 7:
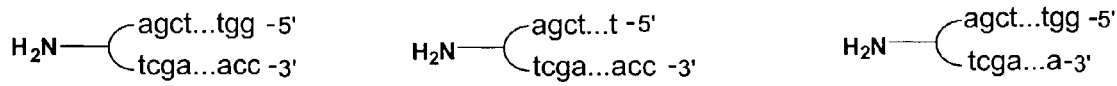

A connector of the present invention includes a bifunctional phosphoramidite [FIG. 7(A)]. This structure is suitable for use in automated oligonucleotide synthesis by procedures known to those of skill in the art [FIG. 7(B)]. A connector phosphoramidite can be introduced in any position of a synthesized oligonucleotide chain to obtain different structures of DNA duplexes, such as: full duplex or partial duplexes with protruding 3'- or 5'-ends [FIG. 7(C.)]. The linker with a free amino-group incorporated into the structure of the connector provides the covalent immobilization of dsDNA probe on matrices supplied with active functional groups (FG) able to react with amino-groups (FIG. 8).

Aspects of a suitable connector include:
  1. Can be synthesized very simply by using inexpensive commercial chemicals. A major cost savings is that enzymes are not needed.
  2. Can be used as a phosphoramidite in the protocol for automated oligonucleotide synthesis known to those of skill in the art.
  3. Is chemically stable during oligonucleotide synthesis and post synthesis procedures.
  4. The bifunctional structure of the connector phosphoramidite allows it to be incorporated in any position of a synthesized oligonucleotide chain to receive variants of DNA duplexes such as:
    Full size duplex,
    Duplex with 3'-protruding end,
    Duplex with 5'-protruding end.
  5. The structure of the connector improves the thermodynamic parameters of DNA duplex formation in comparison with duplexes obtained by hybridization from two separate oligonucleotide chains, and also with hairpin duplex structures (Tchurikov, 1998; Riccelli, 2001). The connector group also guarantees the stability of a duplex because the entropy factor is decreased during duplex formation (Schyolkina, 2000).

The structure of a connector of the present invention is a bifunctional phosphoramidite and is suitable for use in automatic oligonucleotide synthesis known to those of skill in the art. The connector includes a linker group for immobilization of dsDNA probe on a matrix. Factors to be considered for construction of a connector molecule include:
  1. Incorporating chemical groups with different functions from each other (for example, one amino group and two hydroxyl groups) to be able to manipulate the molecule selectively during chemical synthesis of the connector; for example, the synthesis strategy described in Scheme 1, FIG. 6 involved selective protection of the primary-amino group in serinol 4 by a trifluoroacetic group and subsequent protection of one of the hydroxylic functions by the DMTr-group. Then trifluoroacetic group was removed selectively and deblocked amino function was reacted with activated ester of aminocaproic acid 3. Phosphitilation of obtained synthon resulted in the desired connector phosphoramidite 7.
  2. Choosing the length of the linker, which can affect the efficiency of interaction of dsDNA probe on the biochip with target molecule (Carmon, 2002). Derivatives of aminocaroic acid 1 and 2 (see: Scheme 2 on FIG. 6) and diethanolamine 3 were used as base components for obtaining the compound 4. The connector phosphoramidite 4 was used in the procedure of solid phase oligonuceotide synthesis by a phosphoramidite method known to those of skill in the art (Sinha, 1983). Limitations in structure and properties of this connector included phosphoramidite 4 demonstrating low yield of coupling reaction (90% instead of 99%), which is needed for successful results in the synthesis of prolonged oligonucleotides. Insufficient yields were encountered in all different variants of synthesis conditions and programs. Next, the oligonucleotides that contained connector 4 in their composition demonstrated abnormal low stability during the deprotection step, in which ammonium hydroxide is used for removing of N-acylic protective group from heterocycle bases. Therefore, a new connector for dsDNA probe was constructed.

Subsequently, a preferred embodiment was developed as shown in Scheme 1 (FIG. 6), 7. A preferred structure for a connector was obtained from serinol and 6-aminocaproic acid 1 as base substances.

For construction of the new connector (FIG. 6, Scheme 1, 7) serinol 4 and activated ester of N-trifluoroacetyl-aminocaproic acid 1 were used. Efficiency of the elongation step with participation of phosphoramidite 7 in oligonucleotide synthesis reaches more than 98%, estimated by spectorophotometer monitoring of DMTr-cation UV-absorbance, which is correlated with the efficiency of each coupling step in oligonucleotide synthesis. Oligonucleotides containing this connector do not change their structure during ammonium treatment during a deprotection step.

By use of newly synthesized connector 7 DNA duplexes for manufacturing of 3D biochips were synthesized (see Scheme 3 and Scheme 4, FIG. 6). There are structures containing recognition sites for several restriction endonucleases (1–5, Scheme 3, FIG. 6) and also Phage λ operator sites ORI (1 and 2, Scheme 4, FIG. 6).

Chemical synthesis of compound 7 was carried out in the manner shown in Scheme 1 (FIG. 6): The $NH_2$-group of amino acid 1 was blocked by reaction of ethyltrifluoroacetate in methanol (1→2). Then carboxylic group in 2 was converted in activated ester 3 by reaction with N-hydroxysuccinimide and N,N-dicyclohexyicarbodiimide. To obtain compound 5 a one-flask method of synthesis was used. It included sequential reactions of serinol with ethyl trifluoroacetate 4a and 4,4'-dimethoxytritylchloride followed by treatment of methylamine 4d. Resulting O-dimethoxytritylserinol is isolated by column chromatography on silica gel with the yield 64%. Condensation of substances 3 and 4 leads to formation of synthone 6, which gives connector phosphoramide 7 after phosphorylation by use of 2-cyanoethyl diisopropylchlorophosphoramidite. FIG. 11 demonstrates the $P^{31}$NMR spectrum of phosphoramidite 7, which contains a representative signal of P(III) atom in the prospective range (around 150 ppm).

Then, the linear DNA fragment was synthesized by automated solid phase oligonucleotide synthesis carried out from commercial phosphoramidite and connector phosphoramidite [FIG. 7(B)]. After deblocking and purification procedures, a structure was obtained, in which two complementary oligonucleotide chains are joined together by a connector via their 3'- and 5'-ends and can form a duplex. The formation of a duplex structure from synthesized linear fragments was confirmed by melting curves (FIG. 12).

As it was shown in background—nobody before used this chemical structure in the synthesis of oligonucleotides. The connector phosphoramidite L is a new substance in oligonucleotide synthesis and its use is a new method for creating improved nucleic acid duplexes.

Double-Stranded DNA Fragments Synthesized to Have Restriction Sites

The sequences of synthetic DNA duplexes are designed for specific purposes (Scheme 3, FIG. 6), for example, to create different new formats of dsDNA biochips using restriction endonuclease and ligases. The structures 1, 2 and 3 (Scheme 3, FIG. 6) have identical combinations of restriction sites, but they differ in the length and structure of the loops, connecting complementary oligonucleotide chains. These structures are useful to investigate the role and effect of the loop structure on duplex formation and its interaction with the enzymes. Structure 3 also has a fluorescence label (fluorescein isothiocyanate—FITC) to control the restriction reaction on a biochip.

Enzymatic cleavage of duplexes results in protruding ends that are available for further reactions with other dsDNA fragments or oligonucleotides.

Combinations of restriction sites presented herein were not reported previously for use in dsDNA-biochips. However, they are available and used for other purposes.

dsDNA duplexes may be synthesized that contain different restriction sites. The combination of two sequential enzymatic reactions (restriction cleavage and ligation) allows the microarrays to have selected functional parts of genomic DNAs or their combinations.

The sequence of a synthetic DNA duplex (FIG. 9) containing recognition sites for restriction enzymes BamHI and HindIII is an example demonstrating how dsDNA-biochips can be used for creation of new dsDNA biochip format. Enzymatic cleavage of such duplexes 3 by BamHI and HindIII leads to formation of new DNA duplexes 4 and 5 with protruding ends. This step can be controlled by MALDI-MS or by monitoring the loss of fluorescent label incorporated at the cleavage site. Further fluorescent labeled dsDNA fragments 6 and 7 with protruding half-sites BamHI and HindIII can be covalently bonded by DNA-ligase to the duplexes 4 and 5 respectively. Thus, new dsDNA biochips are formed. The appearance of fluorescent signals during this step should indicate that the appropriate reactions proceeded.

Double-Stranded DNA Fragments Synthesized to Have CRO-Repressor Recognition Sites For investigation of specific DNA-protein interactions, several DNA duplexes, containing Lambda phage operator site ORI for specific interaction with CRO-repressor, were designed and synthesized (Scheme 4, FIG. 6).

dsDNA duplexes were obtained in two variants with different structures and different lengths of the loop part of the duplexes to investigate their influence on the binding of CRO-repressor to synthesized duplexes. To control the specificity of dsDNA-protein interactions, two antisense duplexes (Antisense 1 and 2 on Scheme 4, FIG. 6) were synthesized. The antisense duplexes do not contain a specific site for CRO-repressor binding and should be used as a control for non-specific binding of CRO-repressor with double stranded DNA fragments if such binding exists.

The Lambda phage repressor-operator system is used as an example (FIG. 10) for investigations of DNA-protein interaction, which can be carried out with a dsDNA-biochip. For this purpose a dsDNA-biochip can be fabricated with duplexes containing Lambda ORI operator sites and used as a target for fluorescent labeled CRO-repressor to demonstrate efficient interactions of dsDNA probes with the peptide. Then, specificity of protein-DNA interactions in this system is estimated by using a mixture of CRO-repressor with other proteins and further analysis of the effect of administration on the intensity of the fluorescent signal, which appears after target interaction with dsDNA probe. dsDNA biochips with antisense duplexes are used as negative controls in these experiments.

Lambda phage repressor-operator systems are useful as a model for investigation of protein-dsDNA interactions. For example, Lambda operator ORI (dsDNA) can be immobilized on 3D chips. The process of interaction of labeled repressor with dsDNA target is monitored by appearance of fluorescent signal. The specificity of protein-DNA interaction is estimated by measuring change in the intensity of a fluorescent signal during interaction of the repressor and some other proteins with the operator.

3-Dimensional Acrylamide Gel Biochips dsDNA-biochips are constructed using many different kinds of matrices [i.e. supports]. They can be fabricated in 2- or 3-dimensional formats. General requirements for the supports to be used as matrices for fabrication of biochips bearing the dsDNA-probes of the present invention, include the presence of active functional groups that are able to react with free amino-functional groups of the connectors.

Possible variants of covalent immobilization of dsDNA probes on different matrices are demonstrated in FIG. 13. Hydro-gels formed from polysaccharides (for example, dextrane, agarose and others) may form covalent bonds with amino-groups of dsDNA after standard activation by bromocyane 1. The glass surface matrix is modified by 3-aminopropylethoxysilane, and then, sequential treatment of amino-glass surface 2a with phenylendiisothiocyanate and dsDNA probes leads to formation of a microarray 2b. The strategy for immobilization of dsDNA fragments on matrixes 3–5 assumes preliminary modifications of surfaces with carboxylic functions. Silicon 3 is modified by unsaturated acids to obtain 3a, gold 4—by mercaptoacids with formation 4a, magnetic beads is covered by special latex 5a. Formation of covalent (in these cases—peptide bonds) occurs as a consequence of interaction of carboxy-modified matrixes 3a–5a with dsDNA probes in the presence of water-soluble carbodiimide as an activator.

Porous 3-dimensional (3D) substrates, such as polyacrylamide gel pads, posses very good properties to be used as a matrix for DNA chips. These chips have higher capacity and as a consequence—higher sensitivity (U.S. Pat. No. 5,552,270). For these reasons 3D polyacryamide gel pads are suitable as a matrix for manufacturing 3D dsDNA-biochips. Fabrication of 3D dsDNA-biochips was carried out using standard conditions for 3D DNA-biochips (see: Materials and Methods).

Materials and Methods

A. Chemical Synthesis of Connector Phosphoramidite (7) FIG. 6, Scheme 1

1. N-(Trifluoroacetyl)-6-aminocaproic acid (2)

6-Aminocaproic acid (1, 6.55 g, 50 mmol) was suspended in methanol (30 ml) and treated with triethylamine (6.9 ml, 100 mmol) followed by ethyl trifluoroacetate (7.2 ml, 60 mmol). The mixture was stirred at room temperature (r.t.) during 40 hours. The unreacted solid precipitate was filtered, the filtrate was evaporated in vacuo and crystallized from benzene-hexane mixture. Trifluoroacetyl derivative (2) had an 84% yield (9.5 g).

Mp 92–93° C.

2. N-hydroxysuccinimide ester of N-(Trifluoroacetyl)-6-aminocaproic acid (3)

N,N-Dicyclohexylcarbodiimide (7.8 g, 34.4 mmol) was added to a solution of compound 2 (7.1 g, 31.3 mmol) in 100 ml of acetone or tetrahydrofurane (TGF). The reaction mixture was stirred at room temperature overnight. The formed precipitate was filtered and washed with acetone or TGF. The filtate was concentrated in vacuo.

A. The resulting oil was purified by chromatography on a silica gel column using chloroform-acetone (8:1) as a mobile phase. The collected fractions were evaporated to dryness to obtain compound 3 at a yield of 89.7% (9.1 g). C12H15F3N2O5, Mass Spectra (MS): calc. 324.04. found 324.9.

B. Alternatively, the resulting oil was dissolved in ethyl acetate (100 ml), washed with 5% aqueous NaHCO3 (3×50 ml). Organic layer was dried over Na2SO4, filtrated and concentrated in vacuo. The residue was crystallized from isopropanol to give compound 3 with yield 79.8% (8.1 g).

3. 1-O-(4,4'-Dimethoxytrityl)-2-amino-1,3-propanediole (5)

The suspension of serinol (4, 1.82 g, 20 mmol) in 50 ml of methanol, triethylamine (2.77 ml, 20 mmol) and ethyl-trifluoroacetate (3.0 ml, 25 mmol) were added. The mixture was stirred at room temperature for 40 hours and then evaporated. The residue was dried by coevaporation with anhydrous pyridine, dissolved in 40 ml of dry pyridine, and 4,4'-dimethoxytrityl chloride (7.4 g, 22mmol) was added and the mixture was stirred overnight at r.t. Then the solution was evaporated in vacuo and taken up in ethyl acetate (100 ml). The solution was sequentially washed with saturated aqueous solution of NaHCO3 (2×50 ml), water, dried over Na2SO4 and evaporated in vacuo. The residue was dissolved in 40 ml of methanol, then treated with aqueous methylamine (1 h, r.t.) and evaporated. The product was purified by silica gel column chromatography and eluted with chloroform-methanol (8:1). Collected fraction was evaporated to give compound 5 (5.0 g, 64% yield). C24H27NO4, MS: calc. 393.2. found 394.5.

4. N-(Trifluoroacetyl)-6-aminocaproylic derivative of 1-O-(4,4'Dimethoxytrityl)-2-amino-1,3-propanediole (6)

O-Dimethoxytrityl serinol 6 (3.93 g, 10 mmol) and N-hydroxysuccinimide ester 3 (3.56 g, 11 mmol) were dissolved in tetrahydrofurane (25 ml) and the mixture was stirred for 1.5 hours at room temperature. Then the mixture was evaporated in vacuo, diluted with chloroform (50 ml) and washed with aqueous 5% solution of NaHCO3. The organic layer was dried over Na2SO4, filtered and concentrated to dryness. The residue was applied to a silica gel column. Chromatography was performed with chloroform, applying gradient of methanol (1–5%), to give compound 6 (4.5 g, 75%). C32H37F3N2O6, MS: calc. 602.23. found 603.1.

5. Connector Phosphoramidite (7)

To compound 6 (424 mg, 0.7 mmol) in dry dichloroethane N,N-diisopropylethylamine (2.82 ml, 2.8 mmol) was added. The mixture was cooled and 2-cyanoethyl diisopropylchlorophosphoramidite (250 mg, 1.05 mmol) was added with vigorous stirring. The reaction was allowed to proceed at room temperature for one hour. Dry methanol (0.2 ml) was added, the mixture was diluted with dichloroethane (20 ml), and washed with 5% solution of Na2CO3 (2×10 ml) and brine (2×10 ml), dried over Na2SO4, and evaporated in vacuo. The residue was purified on a silica gel column. Chromatography was performed with dichloroethane-ethyl acetate-triethylamine (60:35:5) to give compound 7 (480 mg, 85%).

6. Standardized Chemicals and Equipment for Chemical Synthesis of Connector Phosphoramidite (7)

| | |
|---|---|
| 1. Ethyl trifluororacetate, 99% | Aldrich, Cat# E5,000-0 |
| 2. 6-Aminocaproic acid, 98% | Aldrich, Cat# A4,460-6 |
| 3. 4,4'-Dimethoxytrityl chloride, 95% | Aldrich, Cat# 10,001-3 |
| 4. Triethylamine, 99.5% | Aldrich, Cat# 47,128-3 |
| 5. Methyl alcohol, 99.9% | Aldrich, Cat# 15,490-3 |
| 6. Tetrahydrofuran, HPLC grade | Fisher, Cat# T425-4 |
| 7. Pyridine, 99.8% anhydrous | Aldrich, Cat# 27,097-0 |
| 8. N-Hydroxysuccinimide, 97% | Aldrich, Cat# 13,067-2 |
| 9. 1,3-Dicyclohexylcarbodiimide, 98% | Aldrich, Cat# D8,000-2 |
| 10. Cyanoethyldiisopropylchloro phosphoroamidite | Aldrich, Cat# 30,230-9 |
| 11. 1,2-Dichloroethane, 99.8%, anhydrous | Aldrich, Cat# 28,450-5 |
| 12. Acetonitrile, 99.8%, anhydrous | Aldrich, Cat# 27,100-4 |
| 13. Serinol, 98% | Aldrich, Cat# 35,789-8 |
| 14. N,N-Diisopropylethylamine, 99.5% | Aldrich, Cat# 49,621-9 |
| Cromatographic Silica Gel, 100–200 MESH | Fisher, Cat# S734-1 |
| 16. Ethyl acetate, 99.5% | Aldrich, Cat# 15,485-7 |
| 17. Ammonium hydroxide, 28.0–30.0% | Aldrich, Cat# 32,014-5 |
| 18. Chloroform, A.C.S. | Fisher, Cat# C 298-4 |

B. Chemical Synthesis of Oligonucleotides by Using Liquid Chemical Dispensing Robot
  Standard Protocol
  1. Loading oligonucleotide sequences information for 96-wells plate in computer controlled Liquid Chemical Dispensing Robot (LCDR).
  2. Loading information about the parameters of reaction cycles in the LCDR Computer:
    Injection times for reagent valves;
    Wait times for each step of synthesis;
    Wash cycles after each step;
    Valve assignment for each reagent.
  3. Loading chemicals into the reagent bottles:
    0.075 M solutions of phosphoramidites (dA, dC, DG and T) in acetonitrile;
    0.45 M solution of tetrazole in acetonitrile;
    Capping mixture A (acetic anhydride-lutidine-tetrahydrofurane, v/v 10:10:80);
    Capping mixture B (N-methylimidazole-tetrahydrofurane, v/v 10:90);
    Deblocking solution (3% dicloroacetic acid in dichloromethane);
    Oxidizing solution (0.1 M iodine in tetrahydrofurane-pyridinewater, v/v 60:20:10);
    Acetonitrile.
  4. Filling of 96-wells plate with Control Pore Glass (CPG) Support.
  5. Setting up the machine for a run and automated chemical synthesis of oligonucleotides.
  6. Post processing treatment:
    cleaving synthesized oligonucleotides from CPG support with simultaneous elution by using a 30% ammonium hydroxide solution (1 h under 25° C.);
    deprotection stage in 30% ammonium hydroxide solution (10 h under 25° C. or 5 min in mW-assisted procedure);
    evaporation on SpeedVac centrifuge.
  7. HPLC purification of synthesized oligonucleotides:
    dissolving evaporated crude reaction mixtures in 1.0 ml of 0.05M triethylammonium acetate buffer, pH 7.0;
    filtration
    chromatography on Rainin HPLC System, column C18 (4.6–9.0×250 mm), gradient of acetonitrile in 0.05 triethylammonium acetate buffer, pH 7.0, 25–50%, 8 min;
    evaporation of HPLC elutes on SpeedVac centrifuge.
  8. Final removing of 5'-protecting group by treatment of evaporated oligonucleotides with 80% acetic acid solution during 5 min under 25° C. followed by evaporation on SpeedVac centrifuge and precipitation of oligos by iso-propanol.
  9. Preparation of probes in 96-wells format for immobilization on the acrylamide micro-matrixes:
    dissolving of oligonucleotides in 500 ml of MQ-water (Stock solutions) and preparation of diluted (×100) solutions for UV spectroscopy;
    UV spectroscopy of diluted solutions of oligonucleotides;
    evaporation of stock solutions of oligonucleotides;
    calculation of amount of oligonucleotides based on information from UV spectrums;
    final preparation of oligonucleotide solutions in MQ-water in concentrations appropriate for immobilization on the acrylamide micro-matrixes.

TABLE 1

Materials and Equipment

| Chemicals/Equipment | Manufacturer | Catalog # |
|---|---|---|
| Phosphoramidite | | |
| -dA | Glen Research | 10-1000-10 |
| -dG | | 10-1020-10 |
| -dC | | 10-1015-10 |
| -dT | | 10-1030-10 |
| -5'-Amino | | 10-1936-02 |
| CPG Support | Glen Research | |
| -dA | | 20-2000-10 |
| -dG | | 20-2020-10 |
| -dC | | 20-2010-10 |
| -dT | | 20-2030-10 |
| -3'-Amino | | 20-2957-10 |
| Activator | Glen Research | 30-3100-52 |
| | | 30-3100-57 |
| Acetonitrile | Aldrich | 43,913-4 |
| Acetic amhydride | | 32,010-2 |
| Acetic Acid | | 10,908-8 |
| Ammonium hydroxide | | 38,053-9 |
| Dichloroacetic acid | | D5,470-2 |
| Iodine | | 37,655-8 |
| 2,6-Lutidine | | 33,610-6 |
| 1-Methylimidazole | | 33,609-2 |
| 2-Propanol | | 10,982-7 |
| Pyridine | | 27,097-0 |
| Dichloromethane | | 15,479-9 |
| Tetrahydrofuran | | 18,656-2 |
| | | 40,175-7 |
| Triethylamine | | 47,128-3 |
| Liquid Chemical Dispensing Robot | Avantech | P98363 |
| HPLC system | Rainin | 9920-113 |
| HPLC-column C18, 4.6 × 250 mm | Supelco | 58355-U |
| | Varian | CP29519 |
| 9.4 × 250 mm | Zorbax | 880975.202 |
| CentriVap | Labconco | U28652-00 |
| Centrifuge | Eppendorf | 5415C |
| 96 well plate | BioLogical Brand | p9605 |
| Eppendorf microcentrifuge tubes, 1.5 ml | Fisher | 05-402-24B |
| Syringe filter, 0.2 um pore size | Aldrich | Z25994-2 |

C. Preparation of Acrylamide Micro-Matrices by Photo-polymerization
 1. Preparation of Glass Slides
  (a) Immerse 10 glass slides in 10 M sodium hydroxide in a Wheaton glass-slide container (volume 150 ml) for 30 minutes.
  (b) Rinse with five changes of double-distilled water in a container.
  (c) Immerse 10 slides in concentrated sulfuric acid in container for 30 minutes
  (d) Rinse five times in double-distilled water and allow to stand in double distilled water for 5 minutes then rinse again.
  (e) Remove water drops with nitrogen stream. Dry for 1 h at 60° C.
 2. Treatment of Cleaned Slide with Bind Silane.
 Immerse slides in 3-(Trimethoxysilyl)propyl methacrylate and incubate for 40 h min at 37° C.
 Rinse thoroughly with ethanol and then double-distilled water and dry under a nitrogen stream.
 3. Preparation of Solutions for Aldehyde Matrices
  (a) Composition of 5% polyacrylamide solution 0.5 ml 40% Acrylamide/Bis solution (19:1) 1.82 ml 0.2M sodium phosphate buffer (consists of equal volumes of 0.2M sodium phosphate monobasic monohydrate and 0.2M sodium phosphate dibasic anhydrous pH=6.8, store at 4° C.). 1.6 ml glycerol 0.08 ml monomer I solution (N-(5,6-di-O-isopropylidene)hexyl acrylamide). For monomer I solution add 1 ml MilliQ water to aliquot of monomer I stock (25 mg) located in −8° C. freezer. Aliquot and store these at −2° C. for approximately 1 month.
  (b) filter.
  (c) Prepare solution weekly and store at 4° C. Allow solution to reach room temperature before use.
 4. Assembly of Gel-Casting Cassette.
  (a) Clean mask surface with ethanol.
  (b) Rinse thoroughly with distilled water stream rubbing briskly with lint-free tissue.
  (c) Dry under a nitrogen stream.
  (d) Place spacers (audio tape film) on chrome side of mask; two spacers from both sides and one in the center.
  (e) Place slide over mask and spacers with treated surface facing mask.
  (f) Clamp in place.
 5. Photo-Polymerization (Optimized for 4-Cluster Mask).
 Prepare mixture: 100 μl of above polyacrylamide solution
  0.4 μl Methylene blue (0.04%)
  1.2 μl TEMED
  Vortex 3 seconds
  Degas solution 3 min
  (a) Pipette mixture between the slide and the mask allowing the solution to move between the space by capillary action. Take care that air does not enter the pipette or space. Pipette off excess solution.
  (b) Turn cassette over so that glass slide is underneath the mask. Place in Oriel chamber.
  (c) Irradiate for 300 sec.
  (d) Carefully disassemble the cassette under water using the point of a scalpel to separate the slide and mask (the slide floats free without pressure being placed on the gel elements.) Take care not to scratch mask.
  (e) Rinse 30 seconds under running distilled water and soak in distilled water for 15 minutes
  (f) Air dry in a laminar-flow hood
  (g) Keep in dust-free slide box at room temperature. Matrices can be kept for at least 1 year.
 6. Procedure for Activation (Deprotection) of Aldehyde Matrices
  (a) Place matrix in 2% trifluoro-acetic acid for 10 minutes at room temperature (prepare fresh solution after every 10 microchips).
  (b) Rinse well (5 or 6 times) with filtered distilled water for 1 min
  (c) Wash in distilled water ×3 times then leave 3–5 mins in last rinse and dry 20 min in air.
  (d) Put slide into Repel Silane™ (use fresh solution for each treatment) for one minute.
  (e) Wash with acetone or dichloromethane (15 sec) and then thoroughly with tap-distilled water (15 sec under stream).
  (f) Load oligonucleotides.
  (g) Put microchip into freshly prepared solution of pyridine-borane complex in chloroform (0.1M)(80 ml chloroform/1 ml pyridine borane) and cover chloroform layer with water; (approx ¼ inch) hold 12 hours at room temperature (O. N.)
  (h) Wash microchip with distilled water.
  (i) Place microchip into 0.1M sodium borohydride on microchip for 20 min.
  (j) Wash with distilled water 1 min.
  (k) Heat microchip in 0.1×SSPE with 0.1% SDS at 60° C. for 1 h (50 ml).
  (l) Wash biochip in Hybridization Station for 15 min on a stirrer.
  (m) Wash with distilled water 1 min.
  (n) Dry microchip in a dust-free environment in the air for 20 min.
  (o) The chip is now ready for hybridization. The chip could be kept at room temperature.
 7. Standardized Sources of Chemicals and Equipment
  (a) DEPC-Treated Water (Ambion, cat#9920)
  (b) 0.5M EDTA, pH 8.0 (Ambion, cat#9260G)
  (c) Eppendorf Centrifuge 5417C (Fisher, cat#05-406-11)
  (d) Eppendorf microcentrifuge tubes, 1.5 ml (Fisher, cat#05-402-24B)
  (e) Acetone (Sigma, cat#A4206)
  (f) Guanidine Thiocyanate (Fisher, cat#BP221-1)
  (g) 1M HEPES (Sigma, cat#H4034)
  (h) Hybridization chamber: Probe-Clip Press-Seal Incubation Chamber (Sigma, cat#Z36,157-7)
  (i) Kimwipes (Fisher, cat#06-666A)
  (j) 20×SSPE (Sigma, cat#S2015)
  (k) Tween 20 (Fisher, cat#BP337-100)
  (l) Imaging Chamber (Sigma, cat#Z36,585-8)
  (m) Ultrafree-MC 0.45 μm filter unit (Millipore, cat#UFC30HVNB)
  (n) Triton X-100 (Sigma, cat#T9284)
  (o) Ethyl Alcohol, absolute 200 proof, 99.5%, A.C.S. reagent (Aldrich, cat#45,984-4)
  (p) QIAquick PCR Purification Kit (50) (Qiagen, cat#28104)
  (q) Taq DNA Polymerase (includes 10×PCR reaction buffer) (Amersham Pharmacia Biotech, cat#T0303Z)
  (r) PCR Nucleotide Mix: PCR nucleotide mix (10 mM each dATP, dCTP, dGTP, dTTP) (Amersham Pharmacia Biotech, cat# US77212)
  (s) Sonicated Salmon Sperm DNA, Phenol Extracted (Amersham Pharmacia Biotech, cat#27-4565-01)
  (t) Albumin from bovine serum, 20 mg/ml in water (Sigma, cat#B8667)
  (u) Luer Lok syringe, 60 cc/2 oz, B-D (Fisher cat#14-823-2D)
  (v) Millex-GN 0.20 filter units (Millipore, cat#SLGN025NS)

TABLE 2

Preparation of Complex Buffers

| Buffer | Chemical/ Solvent/ Elementary buffer | Amount | Final Concentration | Comments |
|---|---|---|---|---|
| Wash Buffer | 20 × SSPE buffer | 15 ml | 3xSSPE | Filter by using Millex GN 0.20 Filter and Luer Lok Syringe, B-D, 60 cc/2oz Note: Discard first 5 ml of Wash Buffer when you start filtration Keep at room temperature |
| | Tween 20 | 500 µl | 1% (v/v) | |
| | MQ H2O | 34.5 ml | — | |
| 3xHybridization Buffer | 6 M GuSCN | 50 ml | 3 M | Store at room temperature |
| | 1 M HEPES, pH 7.5 | 15 ml | 0.15 M | |
| | 0.2 M EDTA, pH 8.0 | 7.5 ml | 15 mM | |
| | MQ H2O | 27.5 ml | — | |
| Stripping buffer | Guanidinium thiocyanate | 300 g | 4.9 M | Store solution at room temperature in a bottle with dark glass. Use for 20 stripping procedures (see below) then prepare a new portion. |
| | 1 M HEPES, pH 7.5 | 13.2 ml | 25 mM | |
| | 10% (w/v) Triton X-100 | 5.2 ml | 0.1% | |
| | Distilled water | 250 ml | | |
| Blocking solution | BSA, 20 mg/ml | 200 µl | 13.33 mg/ml | Store solution at −20° C. |
| | Salmon sperm DNA, ~20 A260 U/ml (to prepare, add 5 ml of 10 mM HEPES to a bottle with the DNA) | 100 µl | 6,67 A260 U/ml | |

NOTE:
KEEP ALL BUFFERS IN BOTTLES WITH PLASTIC CAPS

TABLE 3

Materials and Equipment

| Chemicals/Equipment | Manufacturer | Catalog # | Lot# |
|---|---|---|---|
| Acetone | Fisher | A18-4 | 11685 |
| Acrylamide/Bis (19/1) solution 40% | BioRad | 161-0144 | 66767 |
| 3-(Trimethoxysilyl)propyl methacrylate | Aldrich | Z-6030 | 03915TI |
| Pyridine-borane complex | Aldrich | 17,975-2 | 13905MU |
| Glycerol | Sigma | G-7893 | 118H0280 |
| Methylene blue | Merck | 73881 | 51076 |
| Ethyl Alcohol (absolute, 200 proof | Aapec Alcohol and Chemical Co | N/A | 099I15UA |
| Chloroform | Aldrich | 31,998-8 | CO 09980AO |
| Repel Silane | Amersham-Pharmacia-Biotech | 39422 | 17-332-01 |
| Sodium borohydride | Aldrich | 21,346-2 | DU 00220MS |
| Sodium Hydroxide Solid | Sigma | S-5881 | 11K0116 |
| Sodium Periodate (meta) | Aldrich | S-1878 | 11K3644 |
| Sodium Phosphate, dibasic. anhydrous | Sigma | S-9763 | 119H0196 |
| Sodium Phosphate, monobasic monohydrate | Fisher | S-369 | 792237 |
| Sulfuric Acid | Fisher | A300-500 | 994173 |
| Sodium Dodecyl Sulfate | Sigma | L3771 | 83H08411 |
| SSPE, 20X | Sigma | S-2015 | 107H8508 |
| (N-(5,6-di-O-isopropylidene)hexyl acrylamide) | Argonne, custom made | | |
| TEMED | Sigma | T-7024 | 67H0136 |
| Trifluoro-acetic Acid | Aldrich | T6,220-0 | 8K3483 |
| Filter (0.45 um filter unit); Millex-HV 0.4 | Millipore | SLHV 025 LS | |
| Glass slides, 3□ × 1□ Plain; | Corning | 2947 | |
| Mask | Nanofilm, California | | |
| Audio tape film | Radioshak XR 60; Type I | | |

TABLE 3-continued

| Materials and Equipment | | | |
|---|---|---|---|
| Chemicals/Equipment | Manufacturer | Catalog # | Lot# |
| Clamp. Medium Binger clips | Masterbrand | BTM00252 | |
| Oriel Light Source | Oriel Instruments | 92532-1000 | S/N 139 |

DOCUMENTS CITED

Braun, E. et al., (1998) *Nature* 391:775–778.
Brockman, J. M. et al. (1999) *J. Am. Chem. Soc.* 121: 8044–8051.
Broude et al., (2001) *Nuc. Acids Res.* 29:e92.
Bulyk, M. L. et al. (1999) *Nature Biotechnology* 17:573–577.
Carlson R. et al. (1999) *Nature Biotechnology*, 17:536–53.
Carmon, A. et al (2002) *BioTechniques*, 32:410–420.
Jackson et al. (2001) *Current Opinion in Chemical Biology* 5:209–215.
O'Brien, J. C. et al. (2000) *Langmuir* 16:9559–9567.
Riccelli, P. V. et al. (2001) *Nucleic Acids Res.* 29(4): 996–1004.
Sam, M. et al. (2001) *Langmuir*, 17:5727–5730.
Schyolkina, A. K. et al (2000) *Biochemistry* 39: 10034–10044.
Sinha N. D. et al. (1983) *Tetrahedron Lett.*, 24: 5843–5848.
Tchurikov, N. A. et al (1989) *FEBS Lett.*, 257(2):415–418
Yan, F. et al (2001) *Anal. Chem.* 73:5272–5280.
Zhao, X. et al. (2001) *Nuc. Acids Res.* 29(4): 955–959.
U.S. Pat. No. 5,552,270

---

We claim:

1. A nucleotide-matrix connector comprising a bifunctional phosphoramidite and a nitrogen linker atom adapted for connecting to the matrix, the connector having the formula:

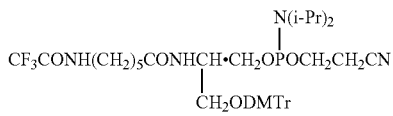

wherein DMTr is dimethoxytrityl and the connector, as part of a nucleic acid strand enables the formation of a synthetic duplex structure and immobilizes the synthetic duplex on the matrix.

2. A nucleic acid comprising strands linked by the connector of claim 1.

3. The nucleic acid of claim 2 is DNA.

4. The nucleic acid of claim 2 is RNA.

5. The nucleic acid of claim 2 is a DNA-RNA hybrid.

6. The nucleic acid of claim 2 is a full duplex.

7. The nucleic acid of claim 2 is a partial duplex with a 3'-protruding end.

8. The nucleic acid of claim 2 is a partial duplex with a 5'-protruding end.

9. The nucleic acid of claim 2 is synthetic.

10. A method for synthesizing a connector designated phosphoramidite of claim 1, said method comprising:
   (a) synthesizing an activated ester of aminocaproic acid by
      (i) protecting the $NH_2$ group of 6-aminocaproic acid with trifluoraccetic protective group; and
      (ii) reacting with N-hydroxysuccinimide and N,N-dicylohexylcarbodiimide;
   (b) obtaining a serinol derivative through
      (i) reacting sequentially with ethyl trifluroacetate and 4,4'-dimethoxytritylchloride and
      (ii) treating with methylamine;
   (c) condensing the serinol derivative with an activated ester of N-trifluoroacetyl-6-aminocaproic acid; and
   (d) phosphitylating the obtained compound with 2-cyanoethyl diisopropylchlorophosphoramidite.

11. A method for constructing double-stranded nucleic acid biochips (microarrays), said method comprising:
   (a) synthesizing at least one double-stranded nucleic acid in which complementary oligonucleotide chains are attached together by the connector of claim 1; and
   (b) attaching the synthesized double-stranded nucleic acid to a matrix through a free-amino group of the linker.

12. A method for constructing a double-stranded nucleic acid microarray, said method comprising:
   (a) synthesizing at least one double-stranded nucleic acid with the connector of claim 1 with at least one specific sequence for restriction endonuclease recognition;
   (b) attaching the synthesized double-stranded nucleic acid to a matrix;
   (c) digesting the attached double-stranded nucleic acid on the matrix using appropriate restriction endonucleases; and
   (d) annealing the digested double-stranded nucleic acid on the matrix with double-stranded nucleic acid fragments having complementary protruding ends; and
   (e) ligating the annealed result of (d).

13. The method of claim 12, wherein the double-stranded nucleic acid is DNA.

14. The method of claim 12, wherein the double-stranded nucleic acid is RNA.

15. The method of claim 12, wherein the double-stranded nucleic acid is a DNA-RNA hybrid.

16. A method for investigating double-stranded nucleic acid-protein interactions, said method comprising:
   (a) synthesizing a double-stranded nucleic acid probe of a specific sequence having a connector as in claim 1;
   (b) attaching the synthesized double-stranded nucleic acid probe to a matrix;
   (c) providing conditions necessary for the double-stranded nucleic acid-protein interaction; and
   (d) determining results of the interaction.

17. The method of claim 16, wherein the double-stranded nucleic acid is DNA.

18. A method for non-enzymatically synthesizing a double-stranded nucleic acid without forming a stem-loop structure, said method comprising:
   synthesizing a linear chain of complementary nucleic acids with the connector of claim 1 at a specific position within the chain; and
   providing conditions necessary for double-strand structure formation from the complementary chains.

19. A method to construct double-stranded DNA microarrays, said method comprising:
   (a) synthesizing complementary oligonucleotide chains bonded together by a novel connector to form a DNA duplex;
   (b) incorporating a linker to the connector, said linker capable of anchoring the DNA duplex to a support; and
   (c) contacting the chemically synthesized duplex-connector-linker molecule to a support.

20. A microchip with dsDNA oligonucleotides each anchored to gel pads by the connector of claim 1.

21. A dsDNA microarray constructed using the method of claim 12.

* * * * *

UNITED STATES PATENT AND TRADEMARK OFFICE
CERTIFICATE OF CORRECTION

| | |
|---|---|
| PATENT NO. | : 7,049,073 B2 |
| APPLICATION NO. | : 10/283670 |
| DATED | : May 23, 2006 |
| INVENTOR(S) | : Chernov et al. |

Figure 1:
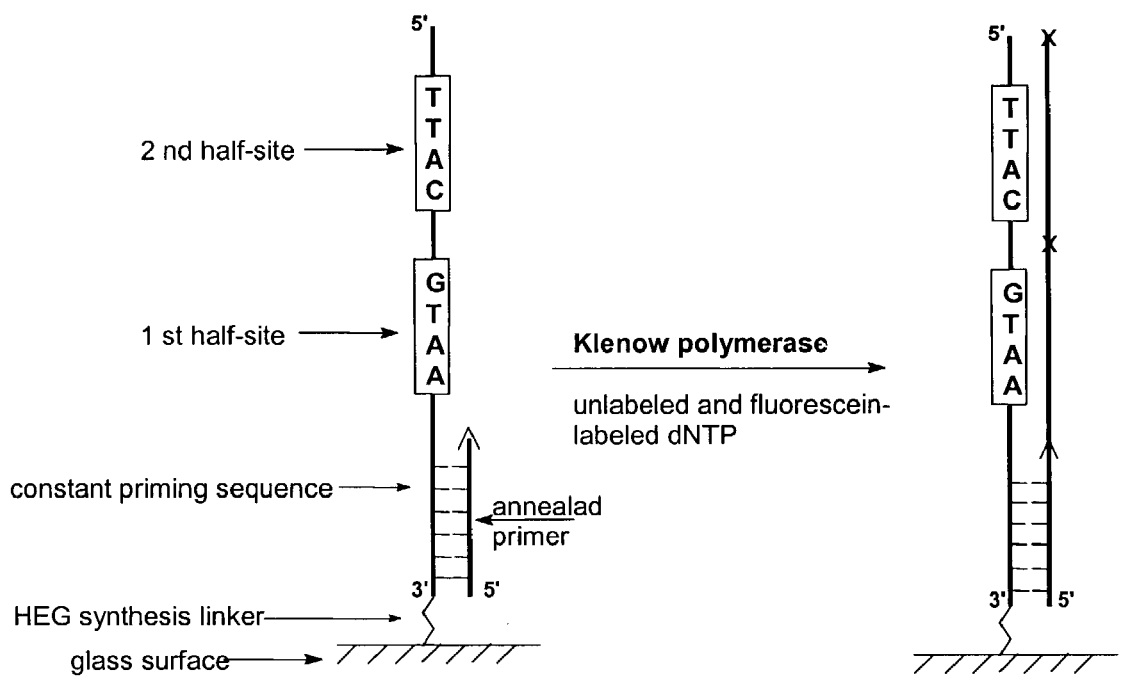
FIG. 1 shows creation of dsDNA array by annealing and further enzymatic extension of the complementary primer (Bulyk et al., 1999).
Figure 2:
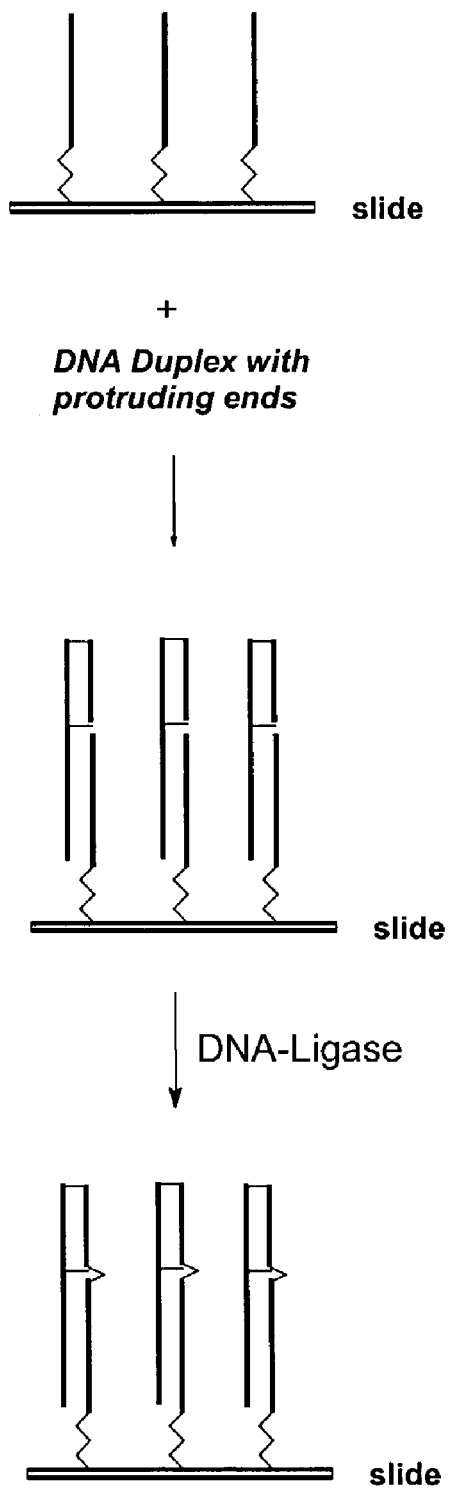
FIG. 2 shows manufacturing steps for surface-coupled dsDNA by hybridization of dsDNA containing a protruding end with a single stranded complement attached to the glass slide surface followed by treatment with DNA-ligase (Braun et al., 1998); protruding ends in DNA duplex means, that one oligonucleotide chain is longer then the other. > shows the ligation point, in which two oligonucleotide chains are connected together by a ligase reaction.
Figure 3:
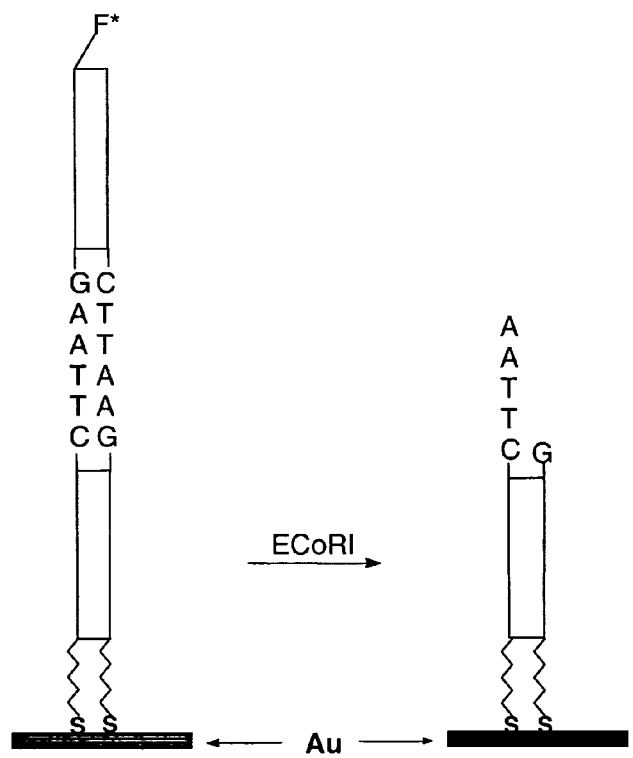
FIG. 3 shows creation of a dsDNA microchip (SEQ ID NO: 1) by connection of self-assembling dsDNA to a gold slide. Disulfide-modified dsDNA 26-mer containing the recognition sequence specific for cleavage by EcoRI restriction endonuclease were synthesized using phosphoramidite chemistry and annealed in solution. Oligonucleotides were labeled with fluorescein (F*) at the 5'-end for use in an optical verification of sequence specific cleavage by EcoRI restriction endonuclease (O'Brien et al., 2000).
Figure 4:
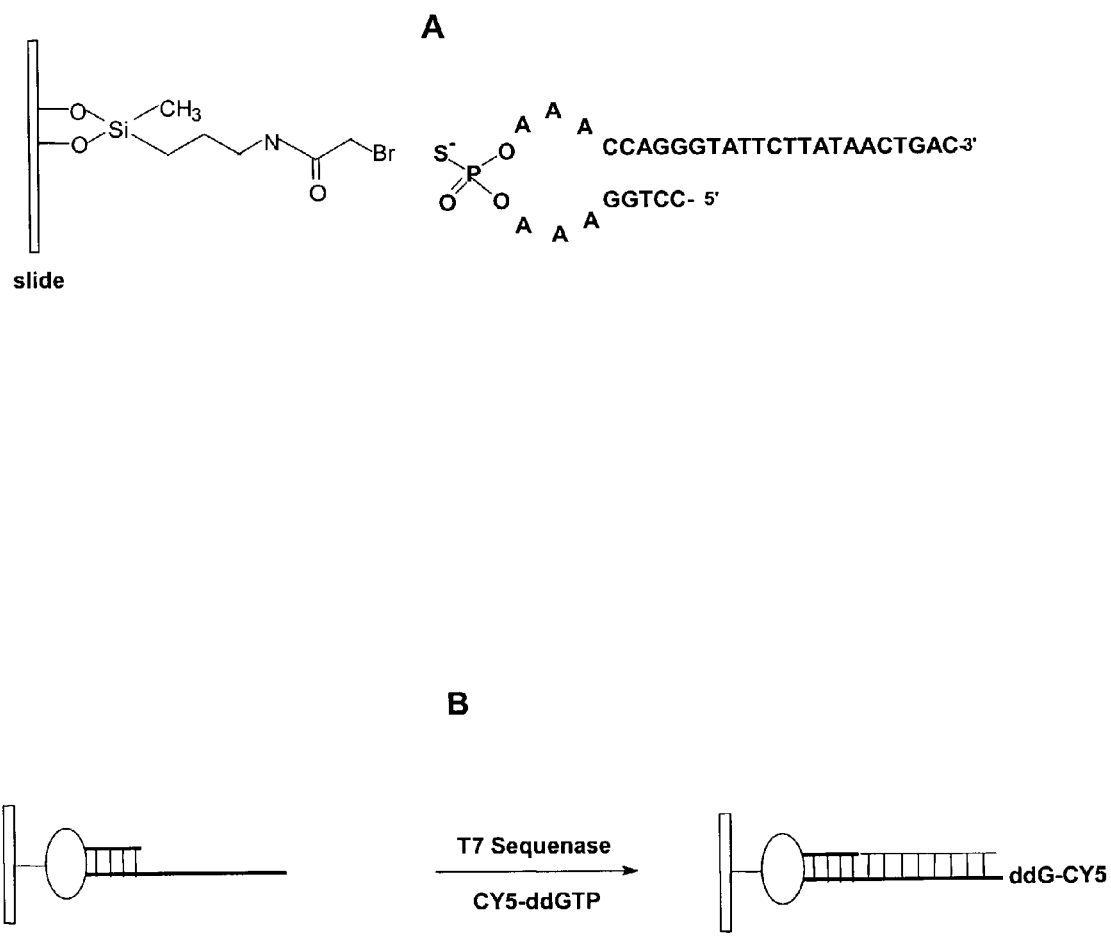
FIG. 4(A) shows a hairpin structure primer with five phosphorothioate groups in the loop comprising six adenosines. The surface of the glass slide is coated with bromoacetamidopropylsilane; (B) shows an arrayed extension of hairpin primer on a glass slide by T7 Sequenase in the presence of dye-labeled ddGTP to obtain full length labeled duplex (Zhao et al., 2001).
Figure 5:
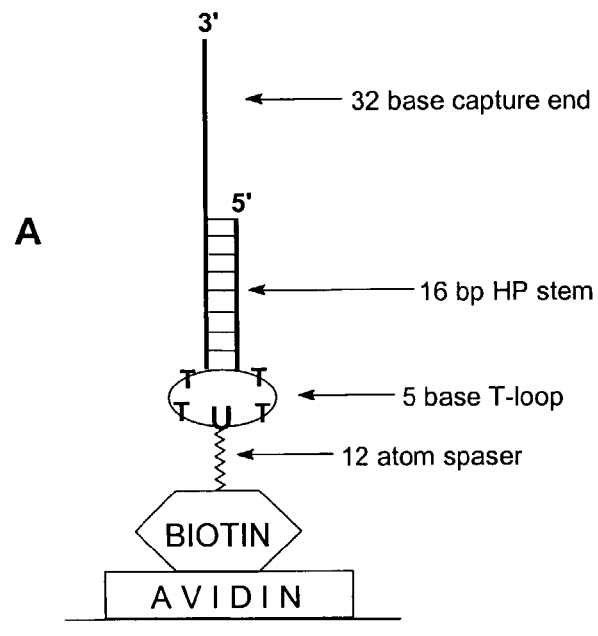
FIG. 5(A) shows creation of a dsDNA chip with a partial duplex structure on an avidin coated microwell surface (Riccelli et al., 2001). Hairpin DNA probes contain biotinylated uracil in the middle of a loop to be captured by avidin; (B) shows an outline of the experiments with stem-loop DNA probes immobilized on a HydroGel (Broude et al., 2001), which were used for searching single-nucleotide mutations by hybridization of labeled targets with hairpin DNA probes followed ligase reaction.
Figure 5:
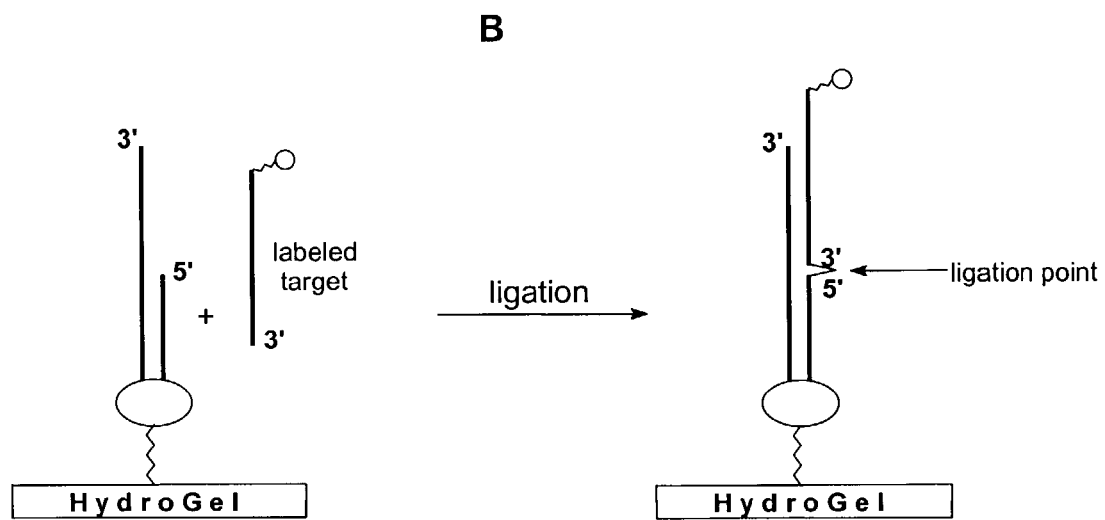

It is certified that error appears in the above-identified patent and that said Letters Patent is hereby corrected as shown below:

Beginning at Column 2, line 66, up to and including Column 4, line 17:

Replace the text beginning at Column 2, line 66, up to and including Column 4, line 17, with the following text:

--which adopt partially duplex stem-loop structures upon denaturing and re-annealing. Stem-loop DNA probes were covalently attached to the matrix by modified nucleosides incorporated in the middle of the loop. The structure obtained was used in hybridization experiments followed by ligase reaction, and the results in searching and analysis of single nucleotide polymorphisms in the p53 gene were reported as good (FIG. 5B).

Another approach for making dDNA microarrays was to use thiol-derivatized 15 base pair duplexes tethered through single 3' and 5' linkages to a gold [Au(III)] surface. The long-range flint structure was measured by scanning probe microscopy. These microarrays are designed for use in nanotechnology or as biosensors. One conclusion of this study was that placement and composition of linkers will affect the film structure of DNA microarrays e.g. 3' duplex linkage results in a flat surface, also linker length and composition may induce different chain-duplex interactions and possibly duplex self-assembly (Sam et al., 2001). Therefore, different tethering methods likely result in different dsDNA microarrays.

Brockman et al. (1999) related a chemical modification procedure to create DNA arrays on gold surfaces for the study of protein-DNA interactions. Surface plasma resonance (SPR) imaging was used. The authors noted that "DNA arrays on glass supports from commercially available sources such as Affymetrix[13] are not a viable option" for SPR imaging investigations of protein-DNA binding interactions (p. 8045, col.1), because this method needs to use DNA arrays on the metal surface. The authors investigated the binding of proteins that are specifically bonded with single-stranded DNA. Both single and double stranded DNA were spotted in a microarray. It was shown, that these proteins bound to single stranded DNA, but only very little bound to dsDNA.

Some goals of microarray DNA molecules, single or double stranded, immobilized on solid supports, are to use DNA chips as films for, e.g. electric charge transport. Jackson and Hill (2001) studied a charge transport through DNA double helices. The presynthesized duplexes were self-assembled onto gold surface, and the resulting films have been characterized by electrochemistry.

For the development of biosensors dsDNA was immobilized on self-assembled avidin monolayer onto a metal surface (Yan and Sadik, 2001). Circular plasmid dsDNA was linearized using the restriction endonuclease *BamHI*. The dsDNA was then biotinylated at single stranded regions. The biotinylated dsDNA was then used as a ligand at a gold electrode covered by avidin. The obtained biosensors were said to be useful to determine small molecular weight organics, that is, a dsDNA based sensor, and for monitoring DNA-analyte interactions.

UNITED STATES PATENT AND TRADEMARK OFFICE
CERTIFICATE OF CORRECTION

PATENT NO. : 7,049,073 B2
APPLICATION NO. : 10/283670
DATED : May 23, 2006
INVENTOR(S) : Chernov et al.

It is certified that error appears in the above-identified patent and that said Letters Patent is hereby corrected as shown below:

Although much effort has been expended in this research area, improvements are needed so that dsDNA microchips can be manufactured efficiently and used effectively.

SUMMARY OF THE INVENTION

This invention describes novel methods and compositions to create double-stranded nucleic acid, e.g. DNA (dsDNA) microarrays. Nucleic acid duplexes are synthesized to include connectors and linkers, and methods for immobilization of the dsDNA to biochips is by novel connectors that include linkers.

The resulting DNA duplexes do not have the cumbersome loops at the point of connection of complementary chains characteristic of some DNA duplexes synthesized in the art and their construction does-not require enzymes. DNA-DNA, RNA-RNA, DNA-RNA, RNA-protein and DNA-protein interactions are investigated using the biochips.

A method for creating dsDNA biochips (microarrays) includes the steps of:
1. synthesizing at least one DNA duplex in which complementary oligonucleotude chains are covalently joined together by a novel connector;
2. attaching the synthesized DNA duplexes to a matrix to form a biochip (microarray) by free amino-groups of linkers incorporated into the connector.

The connector is a bifunctional molecule that can be placed between the two complementary nucleotide chains, which causes the respective strands on each side of the connector to hybridize without a loop formation. The smaller size of the attachment region facilitates the incorporation of more DNA duplexes to the same area of the matrix than would be possible using a stem loop structure. Additionally, this synthesis method does not involve enzymatic reactions, which tend to be more--.

Signed and Sealed this

Twenty-eighth Day of November, 2006

JON W. DUDAS
*Director of the United States Patent and Trademark Office*